(12) United States Patent  (10) Patent No.: US 7,063,531 B2
Maijer et al.  (45) Date of Patent: Jun. 20, 2006

(54) ORTHODONTIC BRACKET SYSTEM

(76) Inventors: Rolf Maijer, 3121 Wessex Close, Victoria, British Columbia (CA) V8P 5N2; Dwight Schnaitter, 10200 Park Meadows Drive, #1818, Littleton, CO (US) 80124; Steve Fillipp, 2011 Ave. C., Lubbock, TX (US) 79404

( * ) Notice: Subject to any disclaimer, the term of this patent is extended or adjusted under 35 U.S.C. 154(b) by 0 days.

(21) Appl. No.: 11/097,225

(22) Filed: Apr. 4, 2005

(65) Prior Publication Data

US 2006/0014116 A1  Jan. 19, 2006

Related U.S. Application Data

(60) Provisional application No. 60/588,399, filed on Jul. 16, 2004.

(51) Int. Cl.
  *A61C 3/00* (2006.01)
(52) U.S. Cl. .............................................. 433/11; 433/8
(58) Field of Classification Search ............... 433/8–17
  See application file for complete search history.

(56) References Cited

U.S. PATENT DOCUMENTS

| 3,464,113 | A | * | 9/1969 | Silverman et al. ............ 433/11 |
| 3,748,740 | A | * | 7/1973 | Wildman ..................... 433/11 |
| 3,772,787 | A | | 11/1973 | Hanson |
| 4,103,423 | A | | 8/1978 | Kessel |
| 4,149,314 | A | | 4/1979 | Nonnenmann |
| 4,248,588 | A | | 2/1981 | Hanson |
| 4,260,375 | A | | 4/1981 | Wallshein |
| 4,337,037 | A | * | 6/1982 | Kurz .............................. 433/8 |
| 4,355,975 | A | * | 10/1982 | Fujita ........................... 433/11 |
| 4,371,337 | A | | 2/1983 | Pletcher |
| 4,492,573 | A | | 1/1985 | Hanson |
| 4,559,012 | A | | 12/1985 | Pletcher |
| 4,582,487 | A | * | 4/1986 | Creekmore .................... 433/8 |
| 4,725,229 | A | | 2/1988 | Miller |
| 4,786,252 | A | * | 11/1988 | Fujita .......................... 433/10 |
| 4,799,882 | A | | 1/1989 | Kesling |
| 4,799,883 | A | * | 1/1989 | Stoller et al. ................. 433/17 |
| 5,094,614 | A | | 3/1992 | Wildman |
| 5,267,854 | A | * | 12/1993 | Schmitt ......................... 433/8 |
| 5,269,681 | A | | 12/1993 | Degnan |
| 5,322,435 | A | | 6/1994 | Pletcher |
| 5,474,445 | A | * | 12/1995 | Voudouris .................... 433/10 |
| 5,516,284 | A | | 5/1996 | Wildman |
| 5,613,850 | A | | 3/1997 | Wildman et al. |
| 5,685,711 | A | | 11/1997 | Hanson |
| 5,711,666 | A | | 1/1998 | Hanson |
| 5,791,897 | A | * | 8/1998 | Wildman ..................... 433/10 |
| 5,857,849 | A | * | 1/1999 | Kurz ........................... 433/10 |

(Continued)

FOREIGN PATENT DOCUMENTS

CA  2304243  5/1998

*Primary Examiner*—Cary E. O'Connor
*Assistant Examiner*—Patrick J. Kilkenny
(74) *Attorney, Agent, or Firm*—Sim & McBurney

(57) ABSTRACT

A novel orthodontic bracket system comprised of orthodontic appliances, such as brackets or buccal tubes, with a vertical instead of conventional horizontal slot orientation. The occlusal-gingival slot orientation minimizes the risk of unintentional debonding of the bracket as a result of insertion and removal of the archwire. An archwire retention mechanism designed to guide, retain and/or seat the archwire. The archwire retention mechanism releases the archwire from the archwire slot whenever appropriate force is applied, or manipulation of physical properties of the material are altered by the operator.

5 Claims, 28 Drawing Sheets

U.S. PATENT DOCUMENTS

| | | | |
|---|---|---|---|
| 5,908,293 A * | 6/1999 | Voudouris | 433/10 |
| 5,913,680 A * | 6/1999 | Voudouris | 433/10 |
| 5,971,753 A * | 10/1999 | Heiser | 433/11 |
| 6,071,119 A * | 6/2000 | Christoff et al. | 433/14 |
| 6,168,428 B1 * | 1/2001 | Voudouris | 433/11 |
| 6,190,166 B1 * | 2/2001 | Sasakura | 433/14 |
| 6,257,883 B1 * | 7/2001 | Voudouris | 433/11 |
| 6,325,622 B1 | 12/2001 | Kelly et al. | |
| 6,361,314 B1 * | 3/2002 | Garton, Jr. | 433/8 |
| 6,663,385 B1 * | 12/2003 | Tepper | 433/11 |
| 2001/0029008 A1 | 10/2001 | Jordan et al. | |
| 2002/0119414 A1 * | 8/2002 | Orikasa | 433/10 |
| 2002/0132206 A1 * | 9/2002 | Voudouris | 433/11 |
| 2002/0197581 A1 | 12/2002 | Georgakis et al. | |
| 2003/0039938 A1 * | 2/2003 | Orikasa | 433/11 |
| 2005/0019719 A1 | 1/2005 | Hanson | |
| 2005/0095549 A1 | 5/2005 | Cinader et al. | |

\* cited by examiner

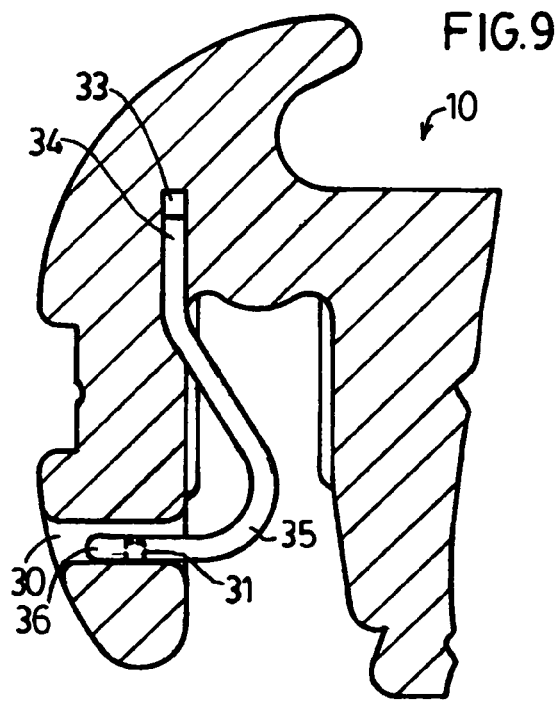
FIG.9
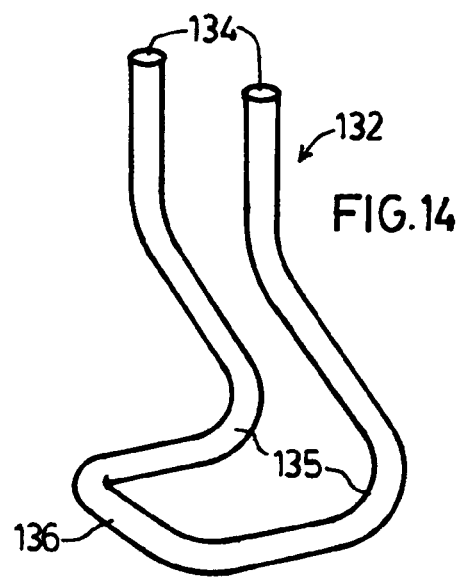
FIG.14
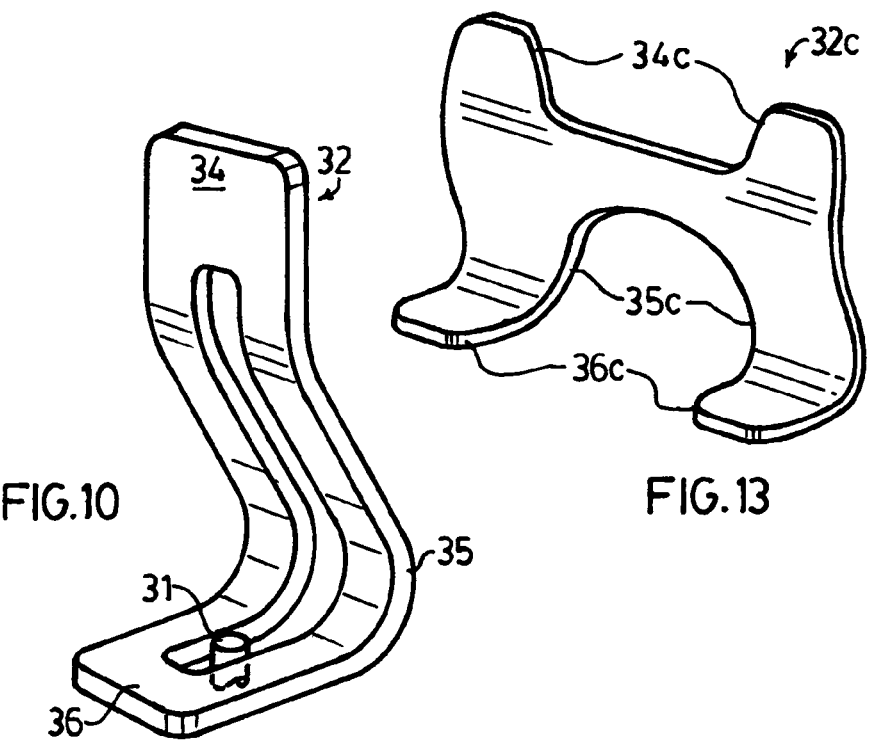
FIG.10
FIG.13

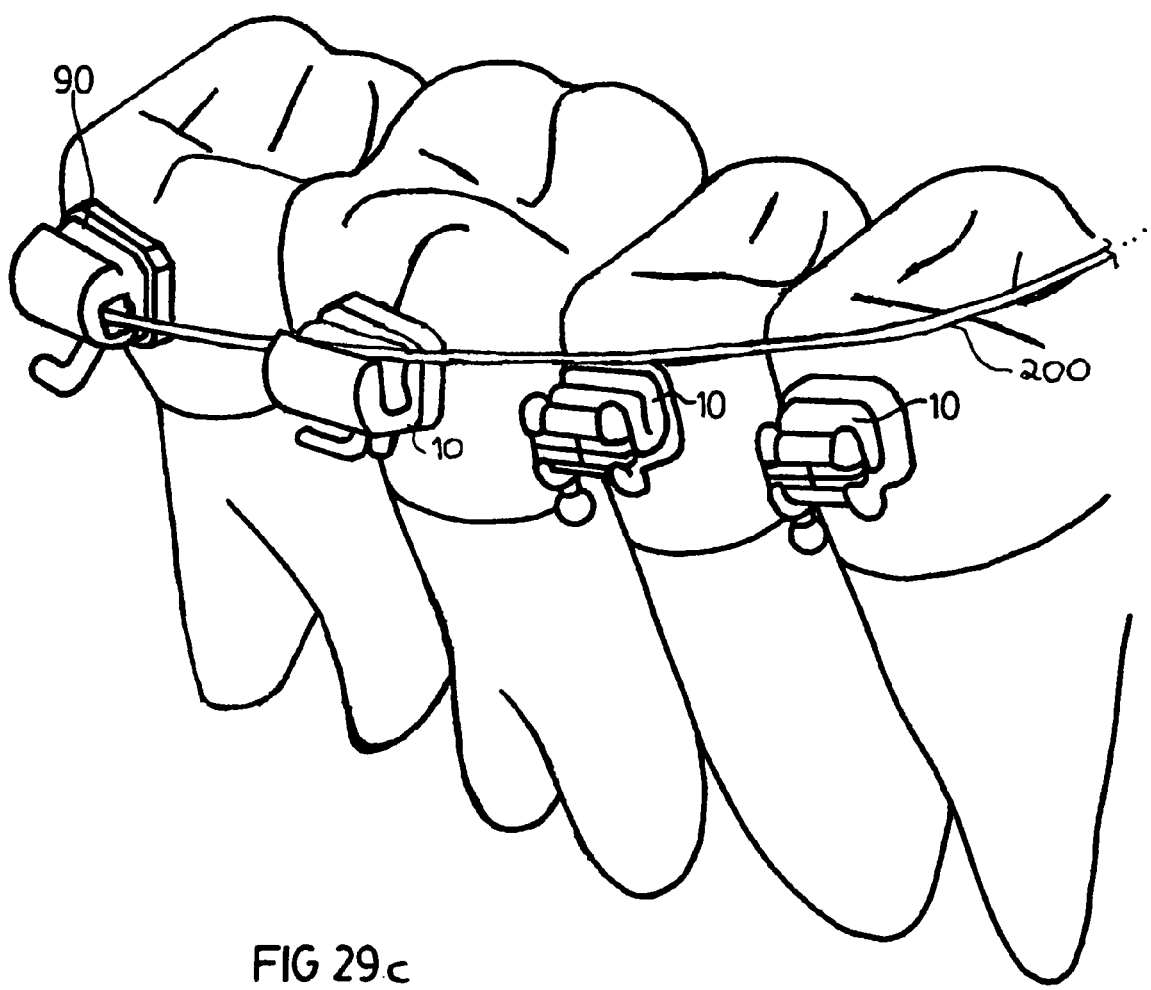
FIG 29.c

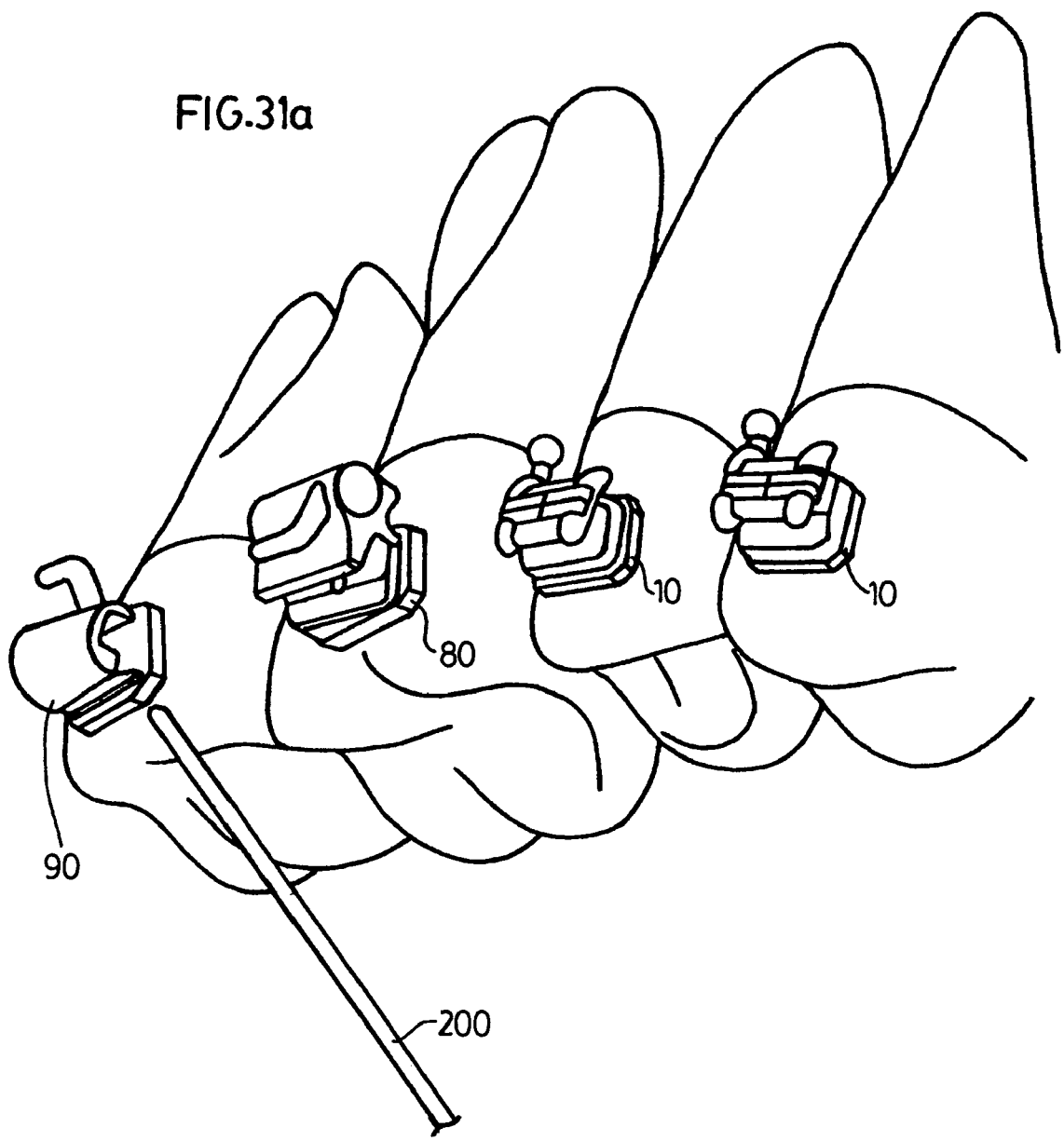

ORTHODONTIC BRACKET SYSTEM

REFERENCE TO RELATED APPLICATION

This application claims priority under 35 U.S.C. 119(e) from U.S. Provisional Patent Application No. 60/588,399 filed Jul. 16, 2004.

FIELD OF THE INVENTION

This invention broadly relates to an appliance primarily but not exclusively used in orthodontic treatment. More particularly, the present invention relates to an orthodontic appliance, such as a bracket or buccal tube, which has a vertical archwire slot and an archwire retention device for retaining and releasing an archwire in the vertical archwire slot.

BACKGROUND OF THE INVENTION

Orthodontic therapy is a specialized type of treatment within the field of dental treatment, which involves movement of malpositioned teeth to functionally improved and correct locations. Orthodontic treatment often improves the patient's occlusion (i.e. bite) and typically enhances the aesthetic appearance of the teeth.

Many types of fixed orthodontic treatment programs involve the use of a set of tiny devices known as brackets and wires that are collectively known as "braces".

Most orthodontic brackets have archwire slots that are open on one side for insertion of the archwire. The typical location of the archwire slot is horizontal, and runs from a mesial to distal location. The wire is inserted from the buccal/labial (i.e., cheek/lip side, referred to sometimes in the art as the "facial" side) to the lingual (i.e., tongue side) direction. The wire is bounded on occlusal (i.e., the side facing the tips of the patient's teeth) and gingival (i.e., the side facing the patient's gingiva or gums) sides by walls or functionally similar structures.

Many orthodontists use ligatures to secure or engage the archwire in the archwire slot. One type of commercially available orthodontic ligature is a small, elastomeric O-ring. Orthodontic O-rings are stretched around small wings (known as "tiewings") that are connected to the bracket body on the gingival side and on the occlusal side of the archwire slot. Once installed, the O-ring ligature extends around the tiewings as well as over the buccal-labial surface of the archwire and exerts pressure on the archwire to reach a fully seated position in contact with a lingual wall of the archwire slot.

Stainless steel ligatures are alternatively used to retain archwires in archwire slots of brackets. The metal ligature is hooked around the tiewings and extended over the labial side of the archwire. End sections of the ligature are then twisted together, and pulled tight to form a loop to retain the archwire in place.

Elastomeric ligatures can suffer from force decay and staining, while metal ligatures often have sharp ends that may retain food, irritate cheek and gum tissue, and increase the risk of infection caused by puncture of an operators tissue through a glove-covered hand.

To solve some of the above mentioned ligation problems, a variety of orthodontic brackets have been proposed having various types of clips or latches for securing the archwire in the bracket. These brackets are commonly known as self-ligating brackets. The latch comprises a clip, spring member, cover, shutter, bail or other structure that is connected to the bracket body for retaining an archwire in the archwire slot. This type of self-ligating securing technique potentially eliminates the need for elastomeric or metal ligatures to secure the archwire. As a result, the time required to secure an archwire or replace an archwire in a self-ligating system is dramatically reduced.

Examples of self-ligating orthodontic brackets having U-shaped ligating latch clips are described in U.S. Pat. Nos. 3,772,787, 4,248,588 and 4,492,573. In general, the clip of such a U-shaped bracket is opened by pushing the latch to an open position with a small-tipped dental instrument. Another example is the Speed™ self-ligating bracket, which has a movable generally U-shaped clip for retaining the archwire.

Examples of self-ligating orthodontic brackets having c-shaped shutters are described in U.S. Pat. No. 6,582,226. Examples of orthodontic brackets with swinging latches are described in U.S. Pat. Nos. 4,103,423, 5,516,284 and 5,685,711.

U.S. Pat. No. 5,711,666 discloses a self-ligating bracket with a latch that comprises a flexible flat spring member. One end of the spring member is fixed to the bracket body on one side of the archwire slot, and the opposite end of the spring member has notches that releasably engage latch sears or catches when the spring member is moved to a slot-closed position. To open the slot, the notches are disengaged from the catches and the spring member is bent to an orientation sufficient to enable the archwire to be removed from the archwire slot.

Other types of self-ligating orthodontic brackets have latches that comprise essentially flat plates that are slidable between a slot-open and a slot-closed position. Examples of such brackets are shown in U.S. Pat. Nos. 5,094,614, 5,322, 435 and 5,613,850. In general, the sliding latches described in these references move in upright channels that are located buccolabially of the archwire slot.

Another type of self-ligating bracket that has been proposed in the past has a latch that is made of a section of wire material that functions similar to a bail. The orthodontic brackets described in U.S. Pat. Nos. 4,149,314, 4,725,229 and 5,269,681 have wire-like latches that swing between a slot-closed position and a slot-open position. The orthodontic bracket described in U.S. Pat. No. 4,260,375 has a wire latch that is slidable between a slot-open and a slot-closed position.

In general, there are three types of tooth movement that are important to orthodontic practitioners. Rotational movement, as its name suggests, is rotational movement of a tooth about its long axis. Tipping movement is another type, where the movement is primarily of the clinical crown, with minimal movement of the root tip. A third type is torquing movement, which can be defined as pivotal movement of the long axis of a tooth in a buccal-lingual direction. Preferably, the appliances selected by the practitioner for use provide precise control over movement of the associated teeth for each type of tooth movement. During the course of treatment, it may be necessary to shift each tooth relative to adjacent teeth in order to provide an aesthetically pleasing result at the conclusion of treatment.

However, known self-ligating orthodontic brackets are not entirely satisfactory because optimal control over torquing movement as described above is often difficult to achieve. Precise control over movement of the teeth is desirable so that each tooth can be shifted as needed to its ideal occlusal orientation. Furthermore, it is desirable that this be done with a minimum of friction on the archwire.

Another problem that has been noted in connection with conventional direct-bonded appliances, including self-ligating brackets, is the possibility that such brackets may spontaneously debond from the patient's tooth when the teeth are severely maloccluded. When the teeth are severely maloccluded or excessive torque is applied, for example, if one of the patient's teeth is located a relatively large distance in a lingual direction relative to adjacent teeth in the dental arch, the archwire must be deformed a significant distance in order to be engaged in the archwire slot. In such instances, the inherent tendency of the archwire to return to its normal arch-shaped configuration may cause the archwire to exert a substantial force and/or torque on the appliance bonded to the severely maloccluded tooth. Unfortunately, the bracket may then debond from the tooth if the archwire exerts a force that is larger than the force required to debond the bracket.

Brackets that spontaneously debond from teeth represent a waste of time and expense for both the practitioner and the patient, and are best avoided if at all possible.

While many types of self-ligating orthodontic appliances have been proposed in the past, there remains a continuing need to improve the state of the art of self-ligating systems. For example, it would be desirable to provide a self-ligating appliance that reduces the time needed for installation of an archwire in comparison to existing self-ligating brackets, so that the time of both the practitioner as well as the patient to complete the installation procedure can be reduced. Commercially available self-ligating systems feature an archwire slot oriented horizontally generally parallel to the occlusal plane. Most of these devices have self-ligating mechanisms, such as latches or hinges, that open and lock in a vertical or horizontal direction to the occlusal plane. Most clip and hinge devices currently commercially available have proven to be difficult to open in the posterior region of the mouth. This is due to the limited working space available between the patients' cheeks and the buccally-oriented entrance of archwire slot. Most of these devices require specially designed instruments or tools to insert the archwire and close the latch or hinge, securing the archwire in the horizontal slot. Other self-ligating systems require a special tool to pry the archwire from the archwire slot releasing it from the horizontal archwire slot of each bracket. Moreover, it would be desirable if such an appliance could provide more precise control over movement of the associated tooth by fully seating finishing archwires in the archwire slot while also facilitating gradual movement of the tooth to its desired ultimate location.

A particular disadvantage of the edgewise bracket self-ligating systems such as those described above is that they lack in truly efficient torque control. Prior art systems are either completely passive (where archwires are never fully seated in the archwire slot), or passive with small-diameter wires and only partially active when full-dimension wires are inserted into the archwire slot and the slot cover engages the inner walls of the slot more efficiently. As a result, prior art self-ligating appliances generally only achieve full-seating and thereby truly efficient torque expression through additional adjustments made to the archwire by the clinician.

U.S. Pat. No. 6,582,226 discloses a number of orthodontic brackets/buccal tubes, each having an archwire slot running across the body in a generally mesial-distal direction with a slot opening in a generally labio-lingual (horizontal) direction. A shutter retains an archwire in the archwire slot. In each of the embodiments shown, the shutter is sufficiently resilient to enable an archwire to be pushed into the slot by a user, while retaining the archwire within the slot until a predetermined minimum force applied by the archwire against the shutter is exceeded. However, the configurations shown are limited to edgewise (i.e., horizontal) bracket systems. They are further limited, by their configuration, to require selection of smaller-diameter wires throughout the entire system, as a larger diameter wire would not be held effectively by the shutter in the case of a severe malocclusion. Furthermore, control and expression of forces, particularly torque, is limited because the configurations only express torque efficiently when a full-sized finishing archwire is in place.

SUMMARY OF THE INVENTION

According to the invention in a general aspect, an orthodontic appliance comprises a base for bonding the appliance to a tooth; a body extending from the base; an archwire slot extending across the body in a generally mesial-distal direction and opening in a generally occlusal-gingival direction; and a resiliently deformable retention device associated with the slot to permit both entry and removal of an archwire from the slot. Because the slot opens in a generally occlusal-gingival direction, the buccal and lingual sides of the archwire slot in this invention are immovable relative to each other, and thereby provide good control over movement of the appliance and the associated tooth whenever torquing, tipping, intruding or extruding of the tooth is desired. The archwire is releasably retained by the retention device in the archwire slot without requiring manual ligation using O-rings, stainless steel ligatures and the like.

Preferably, the retention device comprises a spring for exerting force on a retained archwire having a predetermined minimum dimension against both a lingual and a gingival wall of the archwire slot. The spring is beneficial for providing efficient transmission of force, particularly torque, from an archwire to the tooth via the orthodontic appliance. Retained archwires having less than the predetermined minimum dimension are relatively free to slide within the slot for the initial leveling and aligning phases of treatment.

Still more preferably, the archwire slot is dimensioned to receive and fully seat a ribbon archwire. The ribbon archwire, having an elongated cross-section in a generally occlusal-gingival direction (rectangle or oval, for instance), provides superior torque control when compared with rectangular cross-section wires oriented parallel to the occlusal plane, as used with edgewise slot systems. As such, three-dimensional control of tooth movement is facilitated.

Pressure by an operator on the spring allows the archwire to be released from the vertical archwire slot, whenever a certain force is exerted to the archwire or a force is applied to the spring or springs that exceeds a certain minimum value. The force to release the wire is significantly less than the force required in the same direction to debond the appliance from the tooth, and consequently helps ensure that the appliance will not spontaneously debond from the tooth during the course of treatment.

Use of the spring also ensures that the maximum force exerted by the appliance on the patient's tooth can be limited to a pre-selected, biologically acceptable range. As a result, the amount of discomfort experienced by the patient due to excessive forces exerted by the appliance is also limited. The spring also helps reduce undue force on root portions of the associated tooth so that blood vessels adjacent to the root portions are not adversely affected (i.e. root resorption is reduced).

Other aspects of the invention relate to a self-ligating orthodontic appliance having one or more springs, that fully seat a square, rectangular or other multi-sided wire in the archwire slot maximizing three dimensional tooth control. The springs provide certain advantages when manufacturing the appliance, and also enhances the practitioners control over tooth movement; in particular torque control.

The spring may exert a force in the range of about 2 to 800 Newtons (N) on an archwire in order to retain the archwire in the bracket slot.

Because the retention device releasably retains an archwire without latching, the archwire retention device's spring permits fast, predictable, consistent and efficient insertion and removal of archwires to and from the archwire slot during treatment.

The retention device spring in combination with the pressure of shape memory ribbon archwires allows very light forces to be used to effectively correct the patient's malocclusion. Conventional self-ligating and non self-ligating brackets do not have a spring in combination with ribbon archwires and therefore depend solely on the interplay between the archwire dimension and the overall slot size to effect tooth movement and correct a malocclusion.

Superelastic thermally activated nickel titanium rectangular ribbon archwires, preferably employed herein, with the larger cross section oriented vertically, provide gentle incremental initial torquing forces and more biologically compatible tooth movement in interaction with the archwire retention spring(s).

The brackets are excellent for manufacture as part of a "straight wire" system with preadjusted in/out thicknesses, torque values, rotation values and angulation values to minimize archwire bending necessary to position a patient's teeth ideally.

According to another aspect of the invention, an orthodontic system for receiving an archwire comprises a plurality of brackets, each of the brackets bondable to a respective tooth and comprising: a body; an archwire slot extending across the body in a generally mesial-distal direction and opening in a generally occlusal-gingival direction; and a resiliently deformable retention device associated with the slot to permit both entry and removal of an archwire from the slot. The orthodontic system further comprises second molar appliances for receiving a respective end of the archwire.

The orthodontic system comprising the brackets of the invention works in conjunction with one or more archwires to gradually correct the patient's malocclusion. Due to the configuration of the brackets, an archwire may easily be installed or removed by a clinician.

These and other aspects of the invention are described in more detail below and are illustrated in the accompanying drawings.

BRIEF DESCRIPTION OF THE DRAWINGS

FIG. 9 is a side-sectional view of the bracket of FIG. 2, showing the relationship of the slotted leaf spring with the bracket body and the slot;

FIG. 10 is a perspective view of the slotted leaf spring for the bracket of FIG. 2;

FIG. 13 is a perspective view of an alternative, widened slotted leaf spring, with widened and open-ended slot and generally H-shaped configuration;

FIG. 14 is a perspective view of an alternative retention spring in the form of a wire leaf spring;

FIGS. 31a–31e are bottom-side perspective views of a portion of the self-ligating bracket system on an upper arch, each figure showing a successive stage of archwire installation.

DESCRIPTION OF PREFERRED EMBODIMENTS

Figure 1:
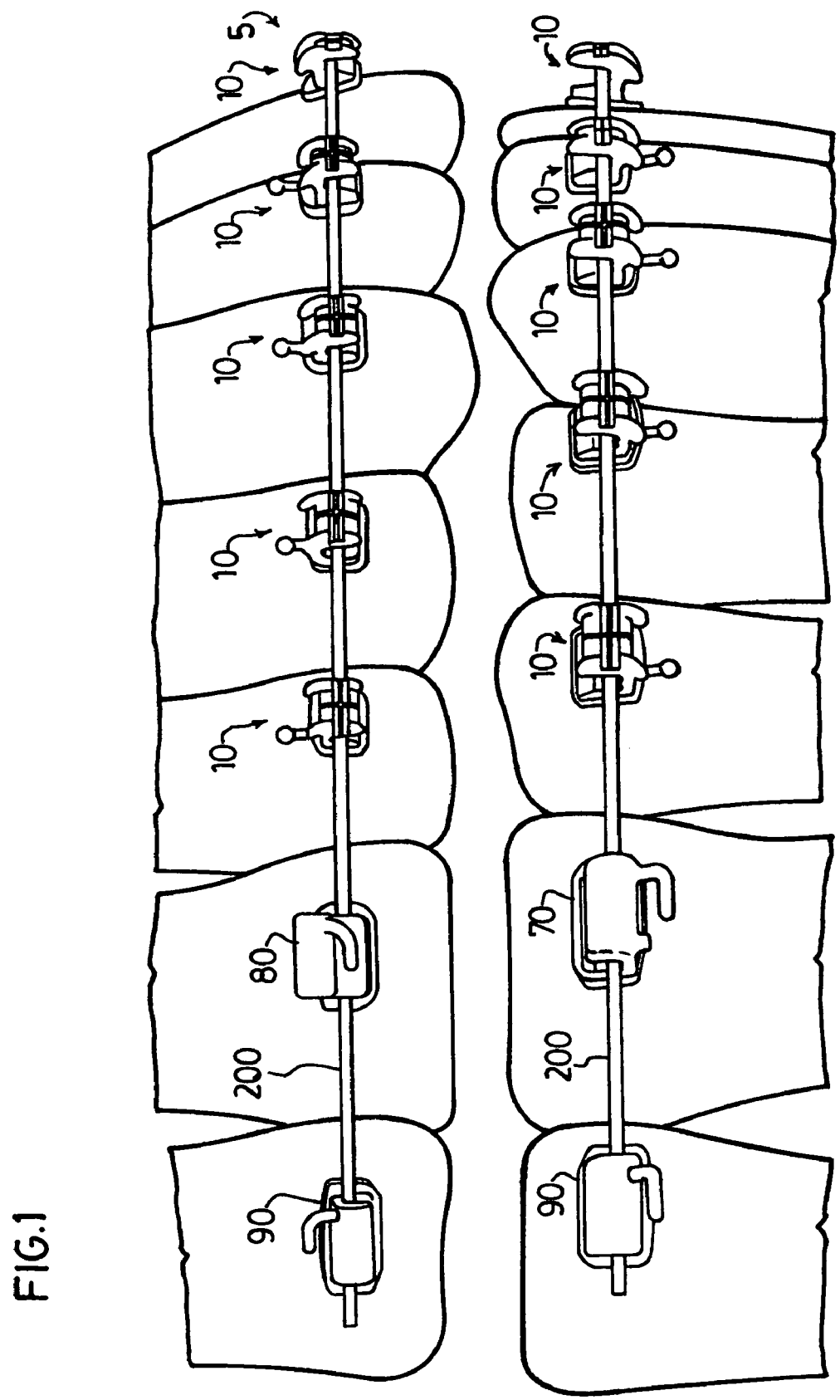
FIG. 1 is a side elevational view of a ribbon arch self-ligating bracket system provided in accordance with one embodiment of the present invention.

Referring to the drawings, FIG. 1 is a side elevational view of a ribbon arch self-ligating bracket system 5 provided in accordance with one embodiment of the present invention. System 5 is comprised of brackets for anterior and posterior teeth on both the upper and lower arch, linked with a ribbon archwire.

Figure 2:
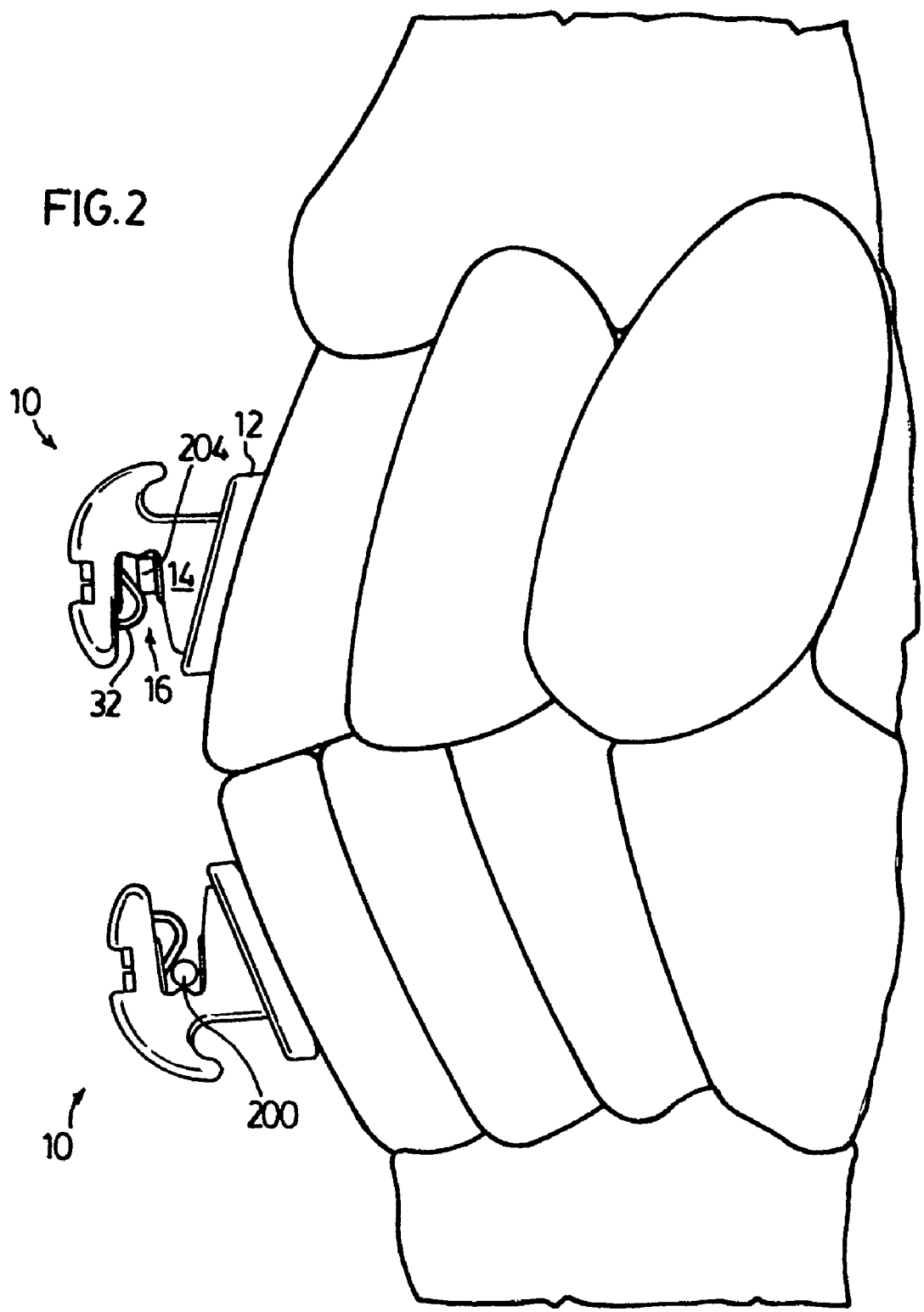
FIG. 2 is an enlarged partial side-elevational view of the bracket system of FIG. 1 showing an upper and a lower anterior bracket.
Figure 3:
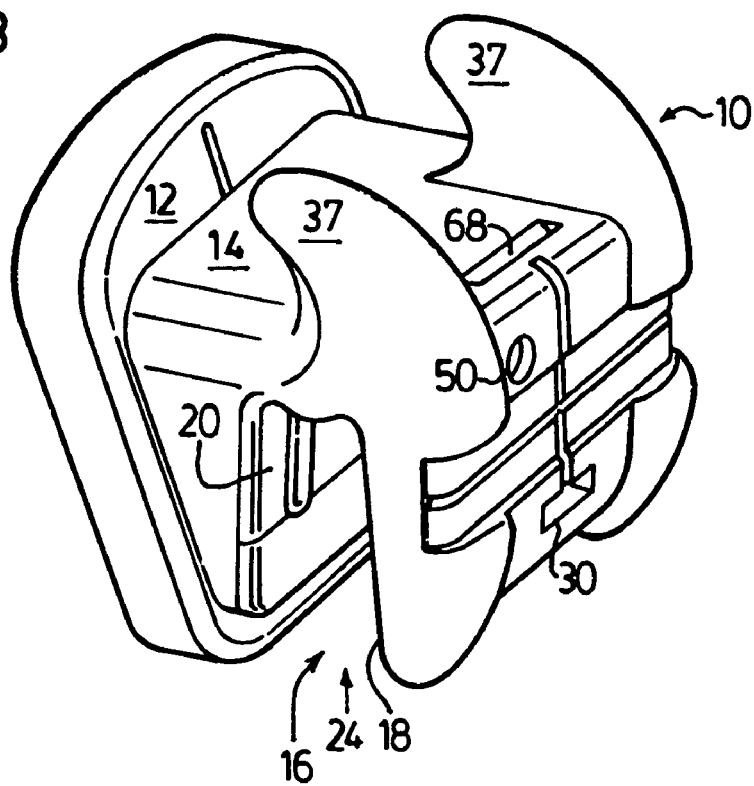
FIG. 3 is a perspective view from above of the bracket of FIG. 2.
Figure 4:
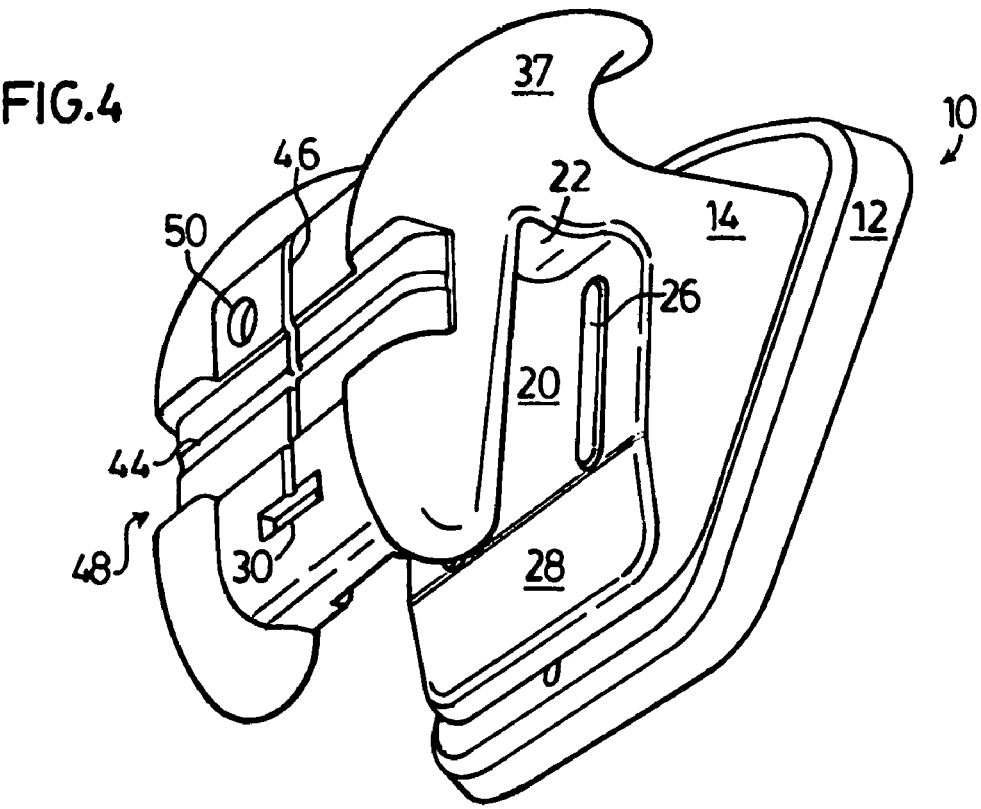
FIG. 4 is a perspective view from below of the bracket of FIG. 2.

FIG. 2 is an enlarged partial side-elevational view of the bracket system of FIG. 1 showing brackets 10 on the upper and lower incisor. FIGS. 3 to 9 show bracket 10 from various angles, both with and without inserted archwires.

Bracket 10 comprises a base 12 and a body 14 extending from the base 12 in a buccal/labial direction. Base 12 is adapted to face and be bonded to a patient's tooth in a known manner, such as a mesh bonding pad, or an integral base.

An archwire slot 16 extends across body 14 in a generally mesial-distal direction. Archwire slot 16 is bounded on three sides by a buccal/labial wall 18, a lingual wall 20, and a gingival wall 22. Archwire slot 16, therefore, has a vertical orientation. According to the embodiment shown, an opening 24 of archwire slot 16 faces in an occlusal direction (i.e. towards the tip of the tooth).

Each of buccal/labial wall 18 and lingual wall 20 have at least one rail 26 extending towards the middle of archwire slot 16 for providing a smaller archwire contact area. Rail 26 in lingual wall 20 also enables improved tooth control by an archwire than if the archwire were seated directly against lingual wall 20. Gingival wall 22 is partially arched in profile, also to provide a smaller archwire contact area.

Lingual wall 20 is beveled in a portion adjacent to slot opening 24 so as to form an entry ramp 28 for ease of insertion of an archwire into archwire slot 16.

A slotted leaf spring 32 is located in archwire slot 16 for releasably retaining an archwire therein. A sectional view of the relationship of slotted leaf spring 32 with bracket 10 is shown in FIG. 9. A perspective view of the slotted leaf spring 32 is shown in isolation in FIG. 10. Slotted leaf spring 32 is made of nickel-titanium alloy, and its gingival end 34 is inserted into a vertically-oriented recess 33 in body 14. Slotted leaf spring 32 is free to move within recess 33. A curved portion 35 of slotted leaf spring 32 connects gingival end 34 to a buccal/labial end 36, and generally arcs through archwire slot 16. Slotted leaf spring 32 then curves away from archwire slot 16 in a generally buccal/labial direction. Like gingival end 34, buccal/labial end 36 of slotted leaf spring 32 is not fixed to body 14. Rather, it is free to move against the bias of slotted leaf spring 32 in a generally buccal/labial-lingual direction along a niche 30 formed in body 14.

Tiewings 37 extend from body 14 and provide other ligation options such as conventional manual ligation using O-rings or the like, if desired by a clinician. There are two tiewings 37 shown on each bracket.

A horizontal reference line 44 is cut or otherwise marked onto a buccal/labial-facing surface of body 14 and, in conjunction with a similarly-formed vertical reference line 46, provides alignment guidance to a clinician when bonding bracket 10 to a tooth. Horizontal reference line 44 denotes the centre of the archwire slot 16 and is placed parallel to the incisal edge of the associated tooth. Vertical reference line 46 denotes the centre of the long axis of the associated tooth. Horizontal reference line 44 and vertical reference line 46 are meant to cross at the theoretical centre of the associated tooth. Height gauge channel 48, also formed in the buccal/labial-facing surface of body 14, is sized and shaped to receive the blade of various commercially available bracket height gauges, as would be understood by one of ordinary skill in the art.

An indentation 50 on the buccal/labial-facing surface of body 14 marks the disto-gingival orientation of bracket 10. Indentation 50 receives a quantum of colored ink. The color of the ink identifies for a clinician in which quadrant bracket 10 is to be used.

Figure 5:
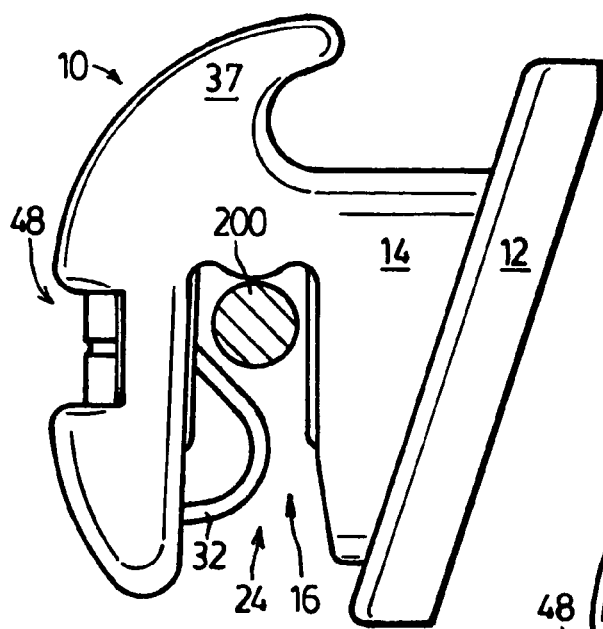
FIG. 5 is a side-elevational view of the bracket of FIG. 2 showing in cross section an inserted round archwire for passive use.

Slotted leaf spring 32 is biased to the rest position shown in FIG. 5 (shown in this case with a round archwire 200), in which opening 24 is partially obstructed, in order to retain an archwire in archwire slot 16. Slotted leaf spring 32 is moveable against its bias by application of sufficient force in a buccal/labial and/or occlusal-gingival direction to a release position, in which opening 24 is sufficiently unobstructed in order to insert or remove an archwire. Because of the configuration of curved portion 35 with respect to archwire slot 16, force exerted by an archwire under influence in a generally occlusal direction against curved portion 35 of slotted leaf spring 32 will cause buccal/labial end 36 to move in a buccal/labial direction through niche 30. Similarly, gingival end 34 will move freely through recess 33. As it moves through niche 30 and recess 33, slotted leaf spring 32 recedes from slot opening 24 thereby allowing the archwire to be removed from vertical archwire slot 16.

In a similar manner, force exerted by an archwire under influence in a generally gingival direction from the direction of opening 24 will cause buccal/labial end 36 of slotted leaf spring 32 to move in the buccal/labial direction through niche 30. Similarly, gingival end 34 will move freely through recess 33. As it moves through niche 30 and recess 33, slotted leaf spring 32 recedes from slot opening 24 thereby allowing the archwire to be inserted into vertical archwire slot 16.

It can be seen that slotted leaf spring 32 cooperates with lingual wall 20 and gingival wall 22 in order to retain an archwire. An archwire of large enough dimensions is fully seated against lingual wall 20 and gingival wall 22 by pressure from slotted leaf spring 32 in both a lingual and a gingival direction due to slotted leaf spring 32 being held against its bias by such an archwire in archwire slot 16.

In the rest position, slotted leaf spring 32 covers up to about 60% of the width of slot opening 24, in order to ease insertion and removal of an archwire. Preferably, a 0.011 inch gap between slotted leaf spring 32 and lingual wall 20 is suitable for retaining archwires as small as 0.014 inches in diameter. Due to the cooperation between slotted leaf spring 32, lingual wall 20 and gingival wall 22, small archwires with, for instance, round cross-section, may be retained within archwire slot 16 without being forced into a fully seated position by slotted leaf spring 32. This enables gradual correction of the tooth. During treatment, archwires of different wire stiffness and sizes may be employed in order to incrementally provide increased expression of the torque, tipping and rotational forces required to move the teeth to their ideal position.

It will be understood that over the duration of treatment, different shaped archwires will be employed in order to efficiently move the teeth as desired.

FIG. 5 shows bracket 10 having received a round archwire 200. Slotted leaf spring 32 retains round archwire 200 in archwire slot 16. Because of the size of round archwire 200, however, slotted leaf spring 32 does not seat round archwire 200 completely in archwire slot 16. Instead, round archwire 200 provides guidance for bracket 10 during tooth movement for initial phases (known as the leveling phase) of orthodontic treatment.

Figure 6:
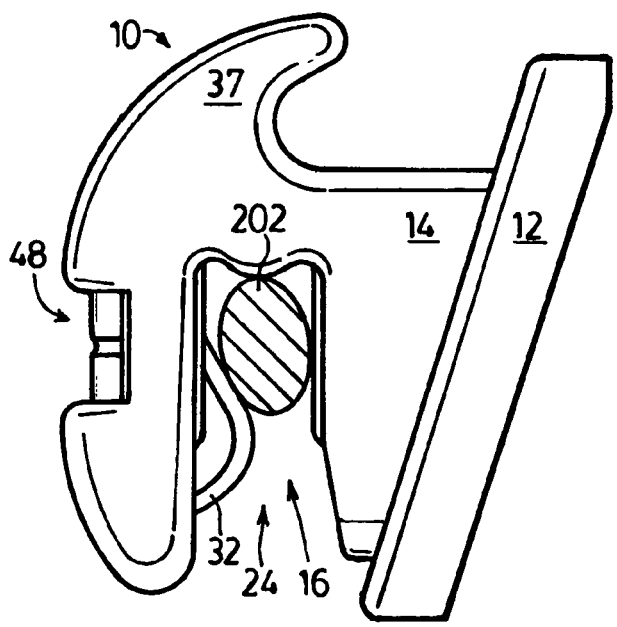
FIG. 6 is a side-elevational view of the bracket of FIG. 2 showing in cross section an inserted oval archwire for commencement of torque expression.

FIG. 6 shows bracket 10 having received an oval ribbon archwire 202. Oval ribbon archwire 202 provides a clinician with gradual control over torquing forces, in particular. Some rotation generally about a mesial-distal axis by oval ribbon archwire 202 is possible as treatment progresses because wire leaf spring 32 enables some degree of both labio-lingual and occlusal-gingival movement of the archwire with respect to the bracket. This provides for leveling, rotation and initial torquing forces while at the same time preventing absolute rigidity and restrictive binding in archwire slot 16.

Figure 7:
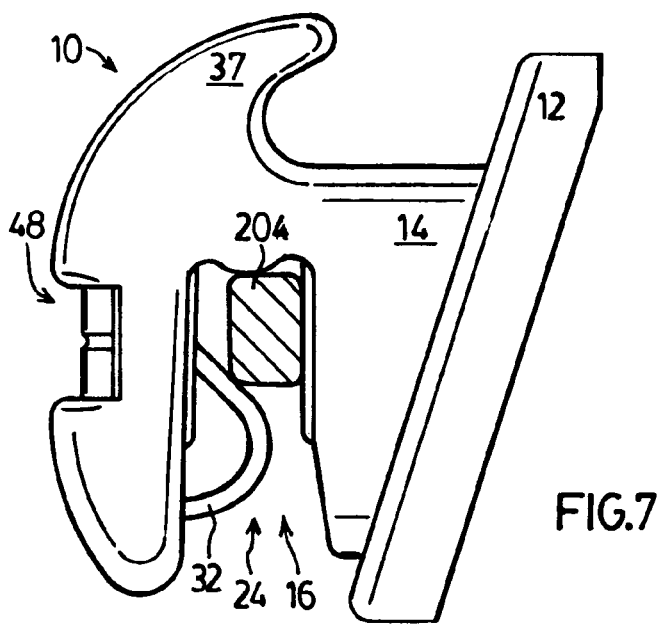
FIG. 7 is a side-elevational view of the bracket of FIG. 2 showing in cross section an inserted rectangular ribbon archwire for increased torque expression.

FIG. 7 shows bracket 10 having received a rectangular ribbon archwire 204. Rectangular ribbon archwire 204 provides a user with still further increased control over torquing forces, in particular. A light constant force is applied by spring 32 against archwire 204, which force gradually expresses the prescriptive torque value of the bracket 10.

Figure 8:
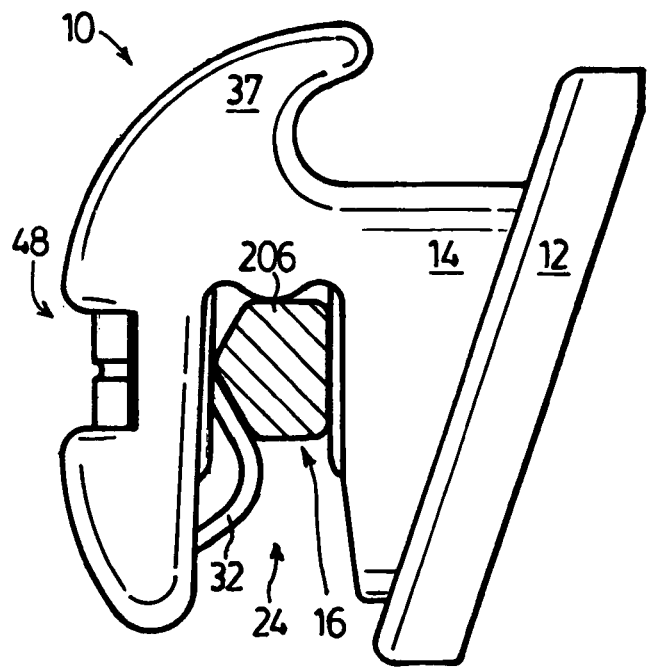
FIG. 8 is a side-elevational view of the bracket of FIG. 2 showing in cross section an inserted five-sided archwire for further increased torque expression.

FIG. 8 shows bracket 10 having received a 5-sided ribbon archwire 206. 5-sided ribbon archwire 206 provides maximum control over torquing forces, in particular. Slotted leaf spring 32 fully seats archwire 206 in archwire slot 16 by exerting spring force in both a gingival and a lingual direction against gingival wall 22 and lingual wall 20, respectively. As would be known, such a 5-sided ribbon archwire 206 is used in the end stages of treatment.

As can be seen, slotted leaf spring 32 has a configuration with respect to the walls of archwire slot 16 that can accommodate different cross-sections and sizes of archwire, while at the same time providing correct seating and therefore correct force expression from an archwire via bracket 10 to the associated tooth.

FIG. 9 is a cross-sectional side view of bracket 10 with slotted leaf spring 32. It can be seen that the edges of niche 30 are rounded for reduced friction, and that slotted leaf spring 32 rests on the occlusal wall of niche 30. Slot recess 33 permits gingival-occlusal sliding of gingival end 34 of slotted leaf spring 32 through slot recess 33 when slotted leaf spring 32 is being forced against its bias. A short post 31 extends vertically from the occlusal wall of niche 30 through the slot of slotted leaf spring 32 to ensure that slotted leaf spring 32 remains loosely coupled to bracket 10 during use. Post 31 is short enough to allow slotted leaf spring 32 to be slid above it through niche 30 when first coupling slotted leaf spring 32 and bracket 10.

FIG. 10 is a perspective view of slotted leaf spring 32, and its relationship to post 31 when in niche 30.

Figure 11:
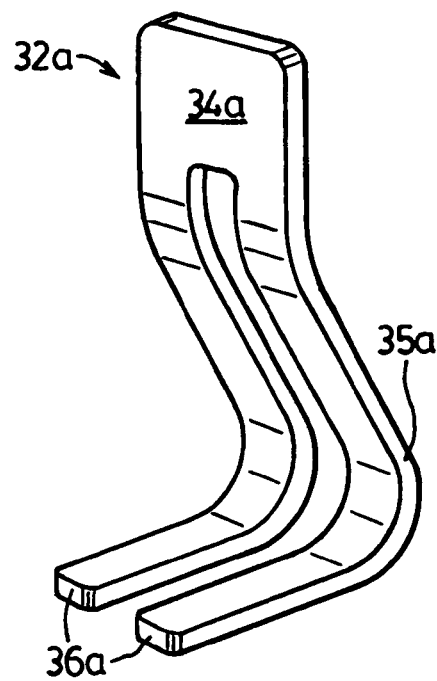
FIG. 11 is a perspective view of an alternate slotted leaf spring with open-ended slot.

FIG. 11 is a perspective view of an alternative slotted leaf spring 32a with a gingival end 34a and curved portion 35a similar to gingival end 34 and curved portion 35 of slotted leaf spring 32 shown in FIG. 10. However, at buccal/labial end 36a of alternative slotted leaf spring 32a, the slot is open-ended. Buccal/labial end 36a may be received in a single niche 30, or in two, smaller niches.

Figure 12:
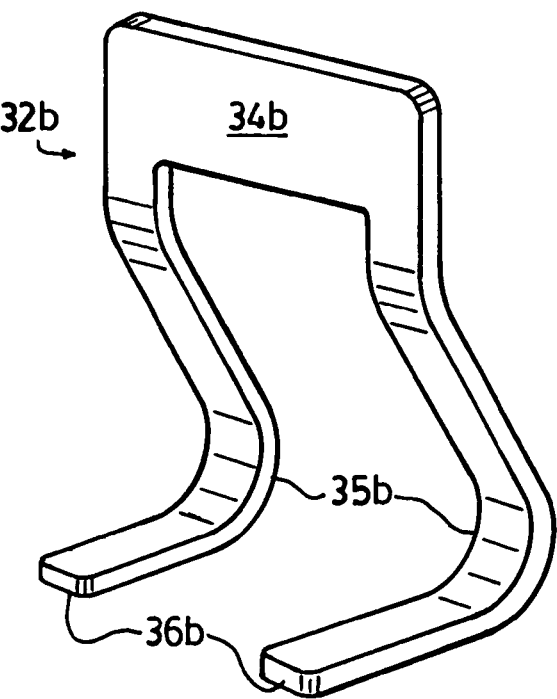
FIG. 12 is a perspective view of an alternative, widened slotted leaf spring, with widened and open-ended slot.
Figure 19:
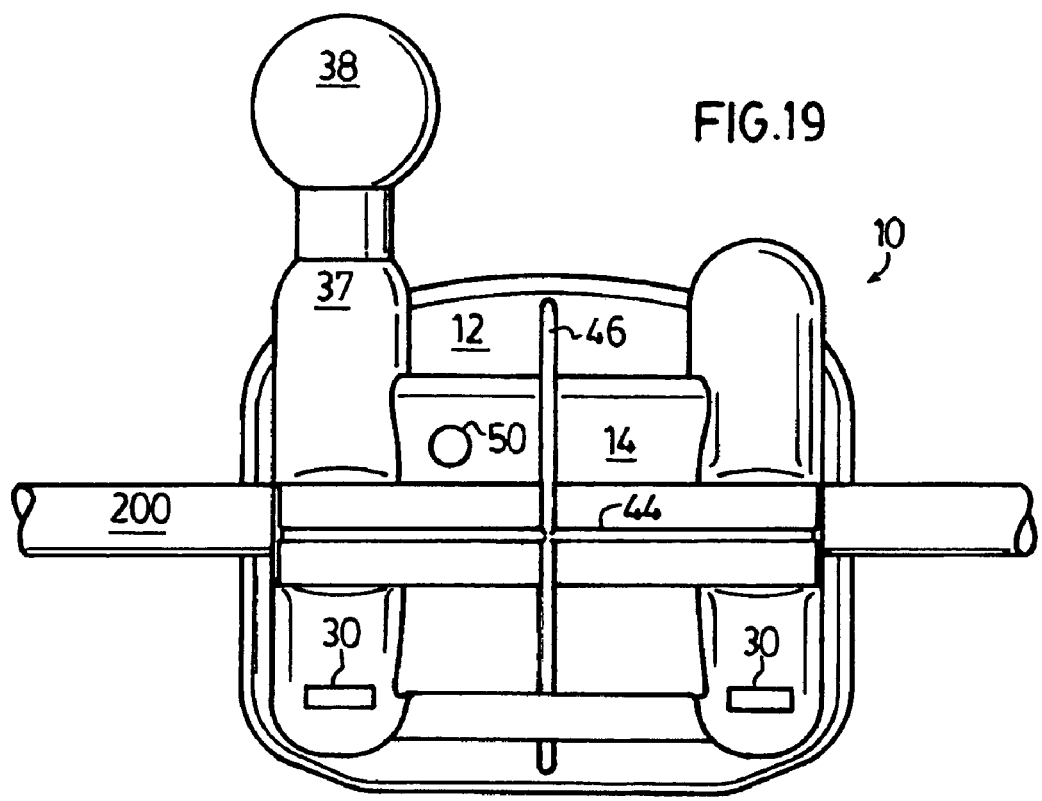
FIG. 19 is a front-elevational view of one embodiment of the bracket showing relationship with inserted round archwire, and having niches for receiving buccal/labial ends of a leaf spring such as that shown in FIG. 12 or FIG. 13.
Figure 20:
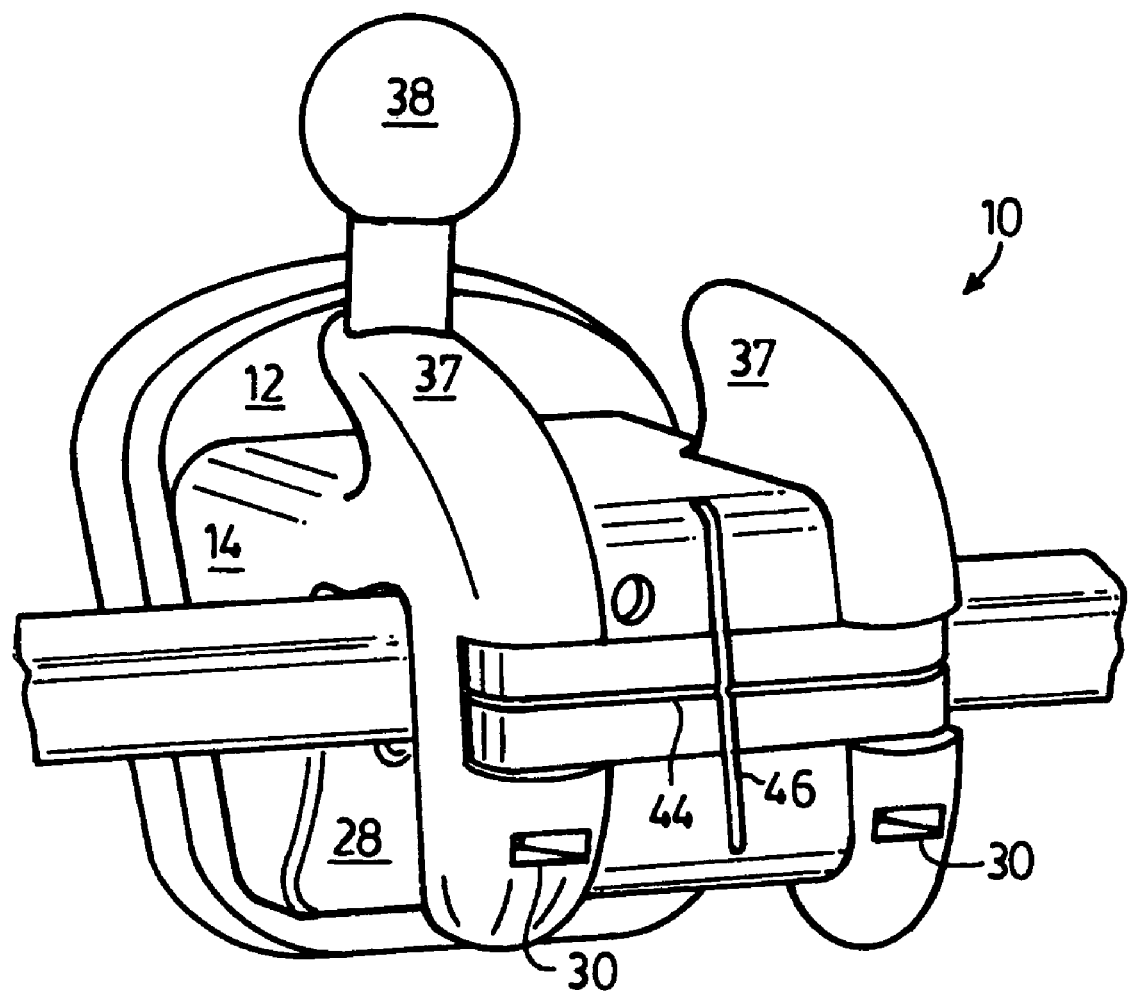
FIG. 20 is a front-perspective view of a bracket similar to that shown in FIG. 19, now retaining a rectangular ribbon archwire and having niches for receiving buccal/labial ends of a leaf spring such as that shown in FIG. 12 or FIG. 13.
Figure 21:
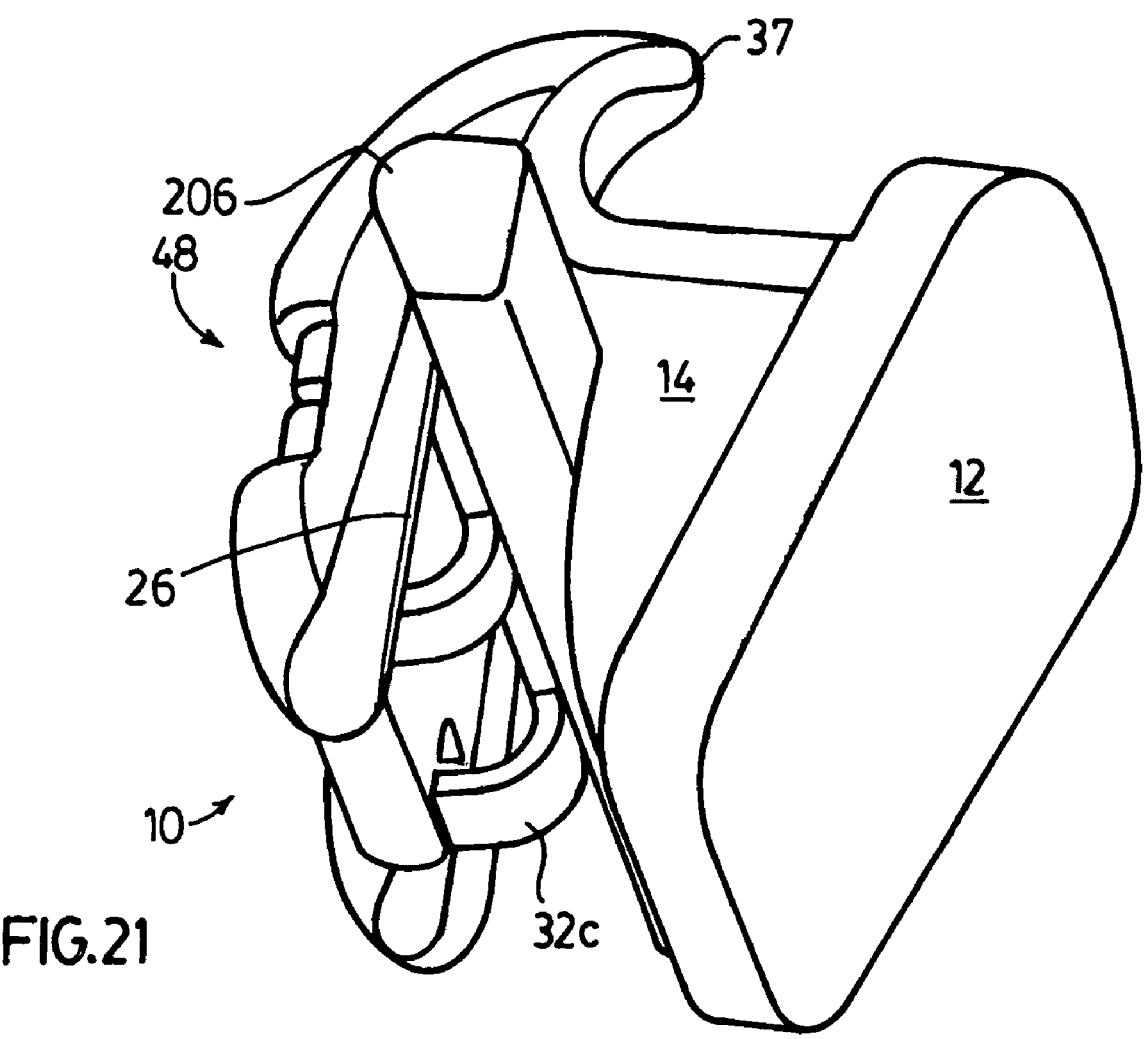
FIG. 21 is a bottom-side perspective view of the bracket of FIG. 20, showing the relationship between a 5-sided archwire and a leaf spring.

FIG. 12 is a perspective view of an alternate widened slotted leaf spring 32b, with a widened and open-ended slot. Gingival end 34b is wider than gingival end 34 of the slotted leaf spring 32 shown in FIG. 11. Also, the slot of the widened slotted leaf spring 32b is wider through curved portion 35b, and is open at buccal/labial end 36b. Buccal/labial end 36b would be received in two niches 30, as shown in FIGS. 19, 20 and 21.

FIG. 13 is a perspective view of another alternate widened slotted leaf spring 32c, with widened and open-ended slot. Gingival end 34c is similar to gingival end 34b of the slotted leaf spring 32b shown in FIG. 12, except gingival end 34c is generally U-shaped rather than flat. Also, through curved portion 35c, the spring slot has an arched shape. These differences give leaf spring 32c a generally H-shaped configuration.

FIG. 14 is a perspective view of an alternative retention spring in the form of a wire leaf spring 132. Gingival end 134 of wire leaf spring 132 is free to move within recess 33. A curved portion 135 of wire leaf spring 132 connects its gingival end 134 to its buccal/labial end 136, and generally arcs through archwire slot 16. Wire leaf spring 132 then curves away from archwire slot 16 in a generally buccal/labial direction. Like gingival end 134, buccal/labial end 136 of wire leaf spring 132 is not fixed to body 14. Rather, it is free to move against the bias of wire leaf spring 132 in a generally buccal/labial-lingual direction along niche 30 formed in body 14. As an alternative to a single recess 33 in body 14, there might be two smaller cylindrical recesses (not shown) for receiving the two portions of the gingival end 134 of the wire leaf spring 132.

Figure 15:
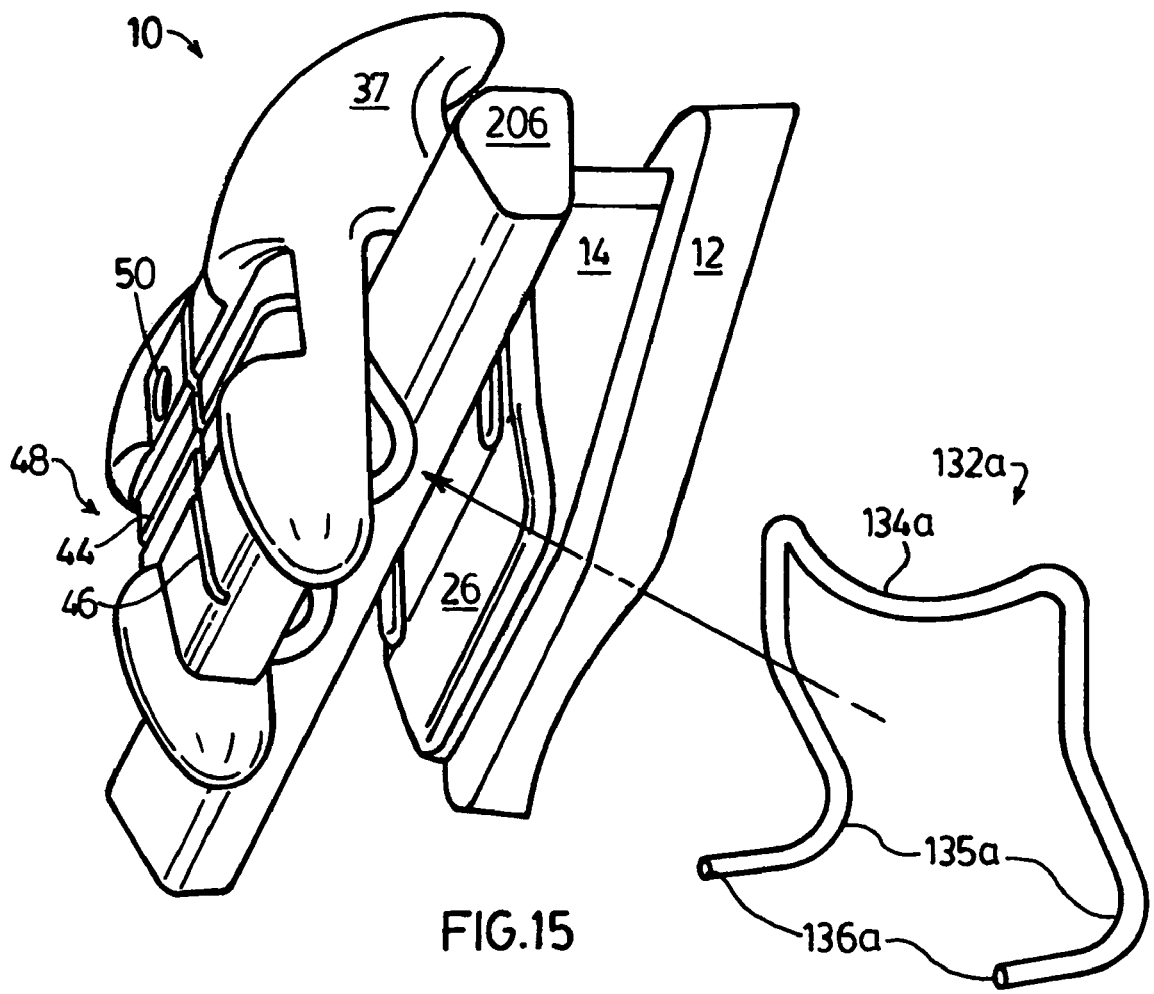
FIG. 15 is a bottom-perspective view of a bracket, showing a second alternative wire leaf spring retaining an archwire.

FIG. 15 is a bottom-perspective view of a bracket 10, showing a second alternative wire leaf spring 132a retaining a five-sided archwire 206. Wire leaf spring 132a has a gingival end 134a, a curved portion 135a and a buccal/labial end 136a. It can be seen that wire leaf spring 132a is similar to alternative slotted leaf spring 32b in that it is wide, and has an open-ended slot configuration. In this example, the portions of buccal/labial end 136a of wire leaf spring 132a move along respective cylindrical niches (not shown) that are similar in function to niche 30 except that they do not extend entirely through the bracket body. Due to its overall width, gingival end 134a is free to move in an occlusal-gingival direction along a wider recess (not shown).

Figure 16:
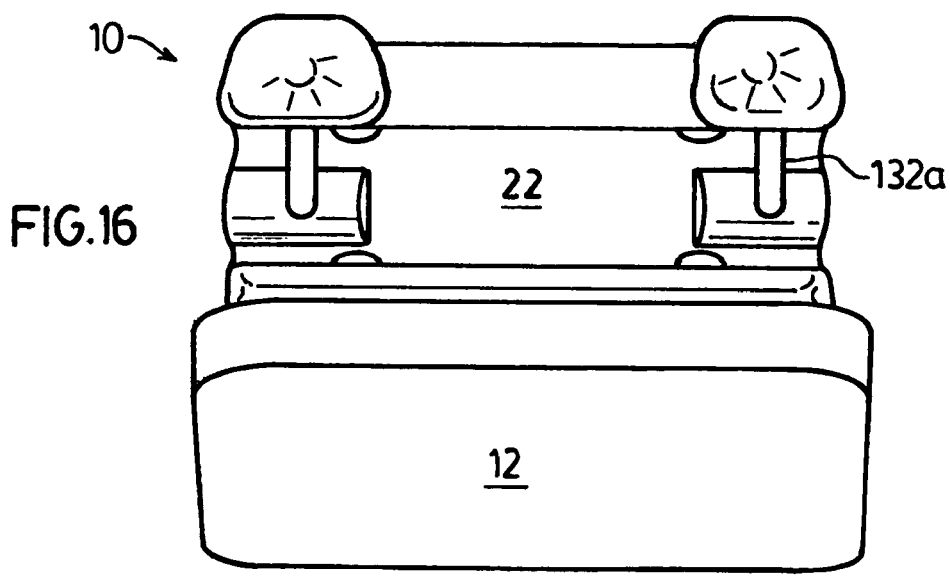
FIG. 16 is a bottom view of the bracket of FIG. 15, showing the arched slot floor and the slot opening partially obstructed by the second alternative wire leaf spring.

FIG. 16 is a bottom view of the bracket of FIG. 15, showing the arched gingival wall 22 of slot 16 and the slot opening 24 partially obstructed by the second alternative wire leaf spring 132a. It can be seen in FIG. 16 that alternative wire leaf spring 132a spans nearly the length of the archwire slot 16, with the wire portions of its buccal/labial end 136a being spaced apart such that they align with respective tie wings 37, rather than between them.

Figure 17:
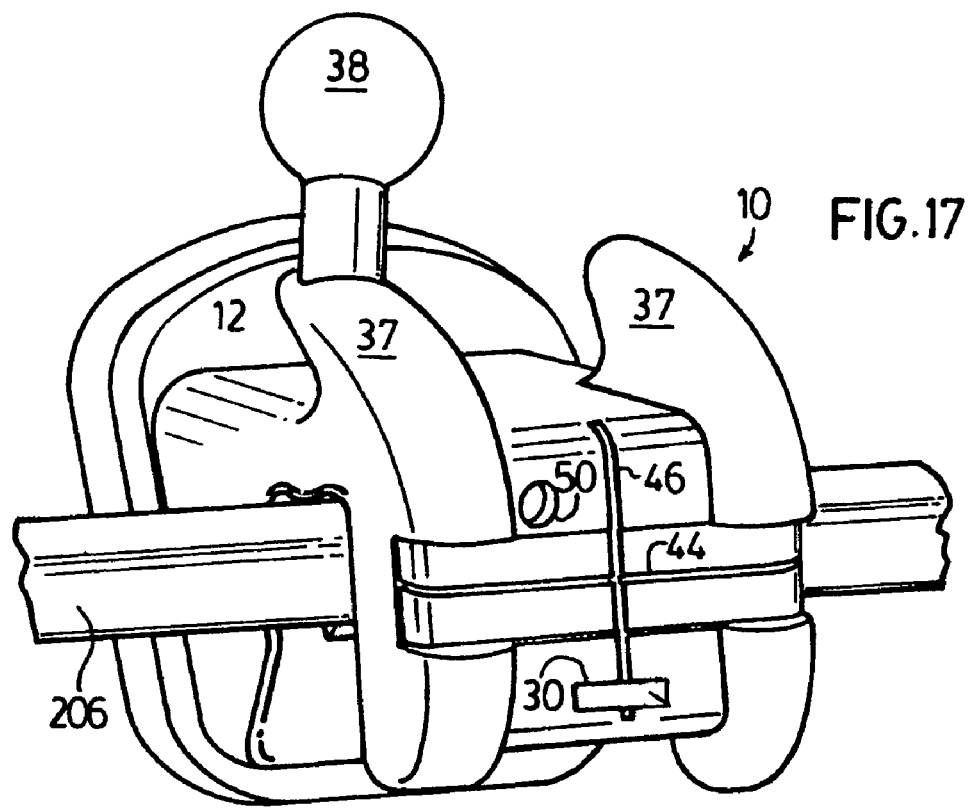
FIG. 17 is a front perspective view of a bracket, according to an embodiment of the invention, showing an inserted five-sided archwire and a hook integral with a tie-wing.
Figure 18:
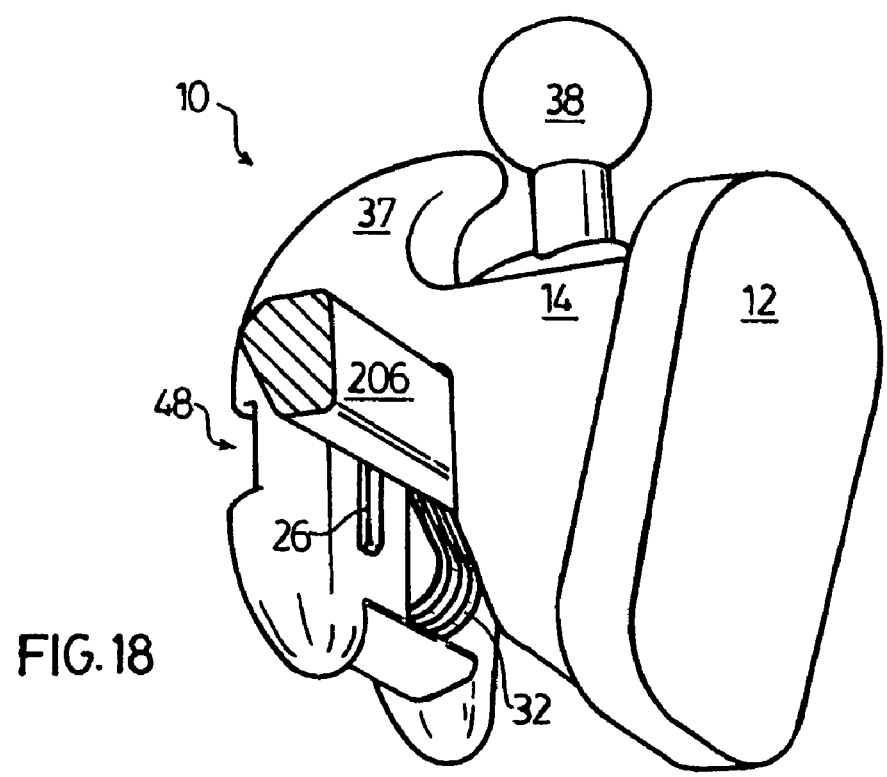
FIG. 18 is a rear-perspective view of the bracket of FIG. 17.

FIGS. 17 and 18 show a bracket 10, according to an embodiment of the invention, showing a 5-sided archwire 206 retained by leaf spring 32, and a hook 38 integral with one of the tie-wings 37. Integral hook 38 provides a hold for auxiliary tooth movement devices such as elastics, coil springs, elastic springs, for example, as would be understood by one of ordinary skill in the art.

FIG. 19 is a front elevational view showing a bracket 10 for anterior use similar to that shown in FIGS. 17 and 18. However, there are two spaced-apart niches 30 instead of a single niche 30. In this embodiment, therefore, an alternative slotted leaf spring such as that shown in FIG. 12 or FIG. 13 is employed. In FIG. 19, a round archwire 200 is being retained.

FIG. 20 is a front perspective view of the bracket 10 shown in FIG. 19, retaining a rectangular ribbon archwire 204.

FIG. 21 is a bottom-side perspective view of the bracket 10 shown in FIG. 19, retaining a 5-sided archwire 206.

Figure 22:
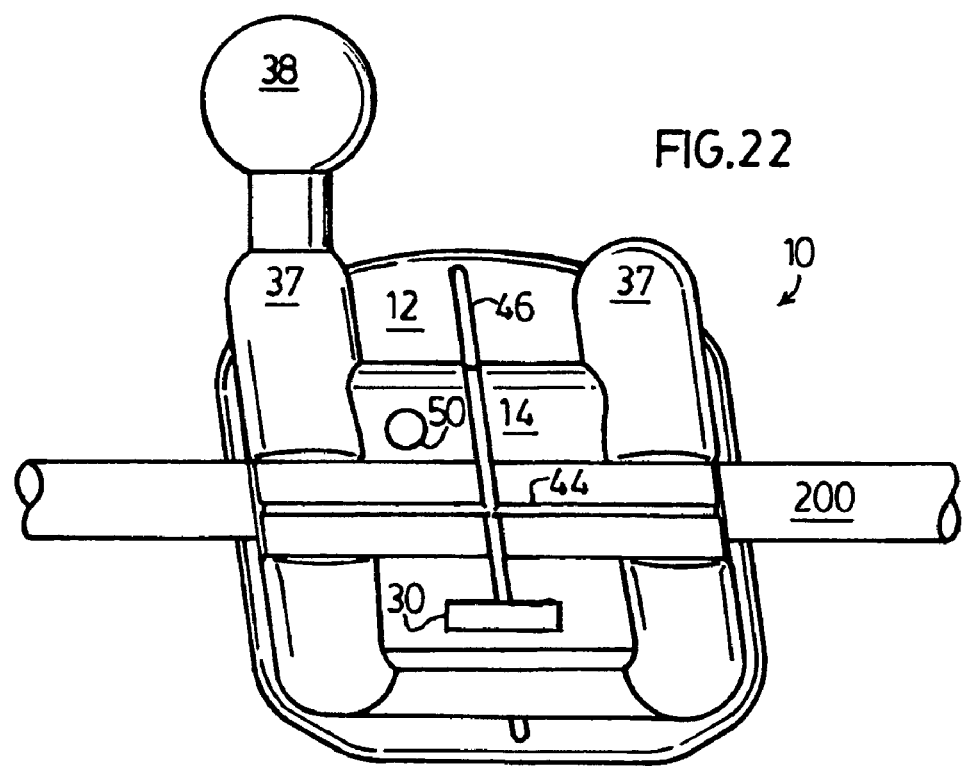
FIG. 22 is a front elevational view of an alternative bracket similar to that shown in FIG. 17.

FIG. 22 shows an alternative bracket 10 for anterior use having a generally trapezoidal shape. According to this embodiment, archwire slot 16 is not perpendicular to "vertical" reference line 46. In FIG. 22, a round archwire 200 is being retained.

Figure 23:
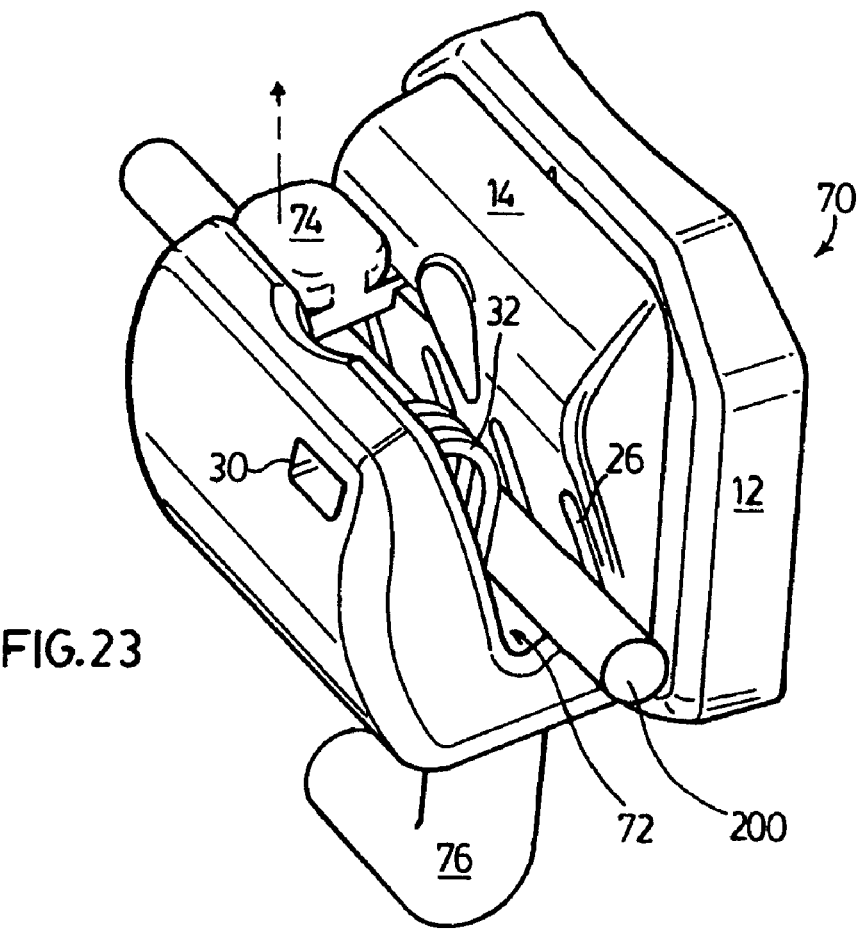
FIG. 23 is a top-side perspective view of an embodiment of the lower first molar bracket.
Figure 24:
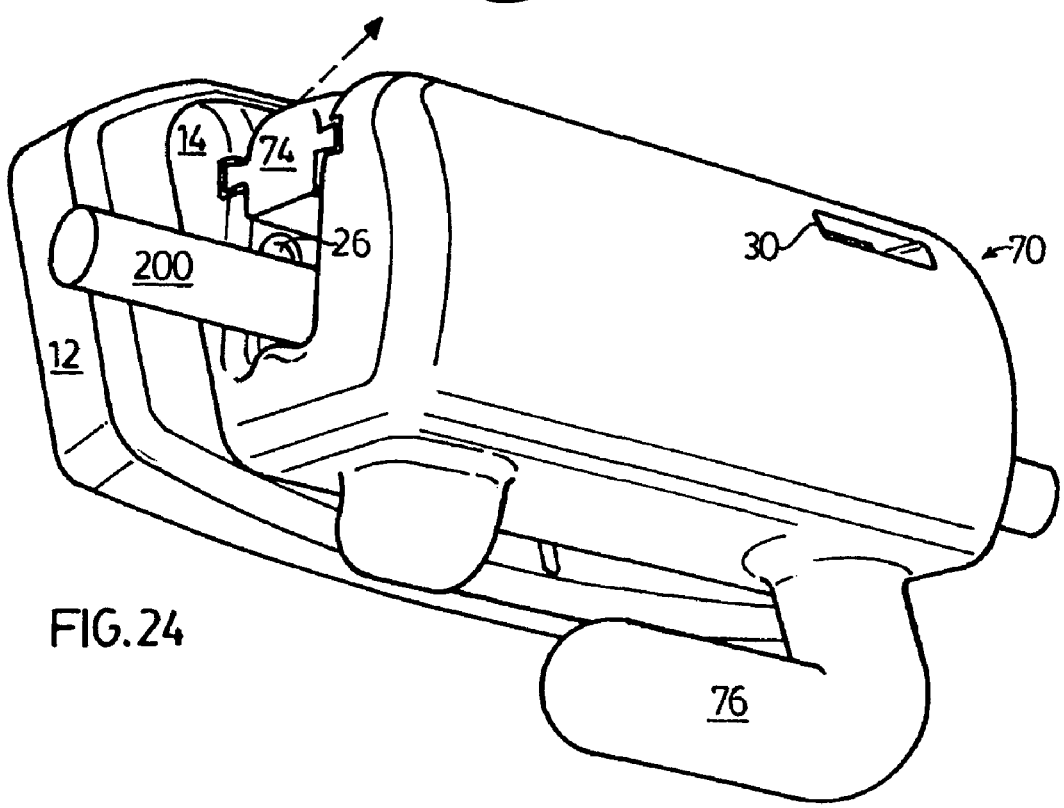
FIG. 24 is bottom-side perspective view of the lower first molar bracket of FIG. 23.

FIGS. 23 and 24 show a lower $1^{st}$ molar bracket 70 with a convertible buccal tube 72 by virtue of a convertible cap 74. Convertible cap 74 is a removable element that has been attached to the bracket 70 by tack welding or soldering during its assembly process. The convertible buccal tube 72 is very useful for en masse archwire insertion and removal prior to placing the second molars in treatment. Once the $2^{nd}$ molar brackets 90 are used in treatment, convertible cap 74 may be removed from the $1^{st}$ molar brackets 70, thereby making the entire slot amenable to insertion of an archwire in the second molar bracket 90. The archwire ends may be inserted into the $2^{nd}$ molar tubes and the archwire inserted into the remaining brackets in the occlusal-gingival direction into open archwire slots 16, as will be described below. Also shown is hook 76 used for auxiliary traction with one or more elastics or retraction coils, as would be understood by one of ordinary skill in the art.

Figure 25:
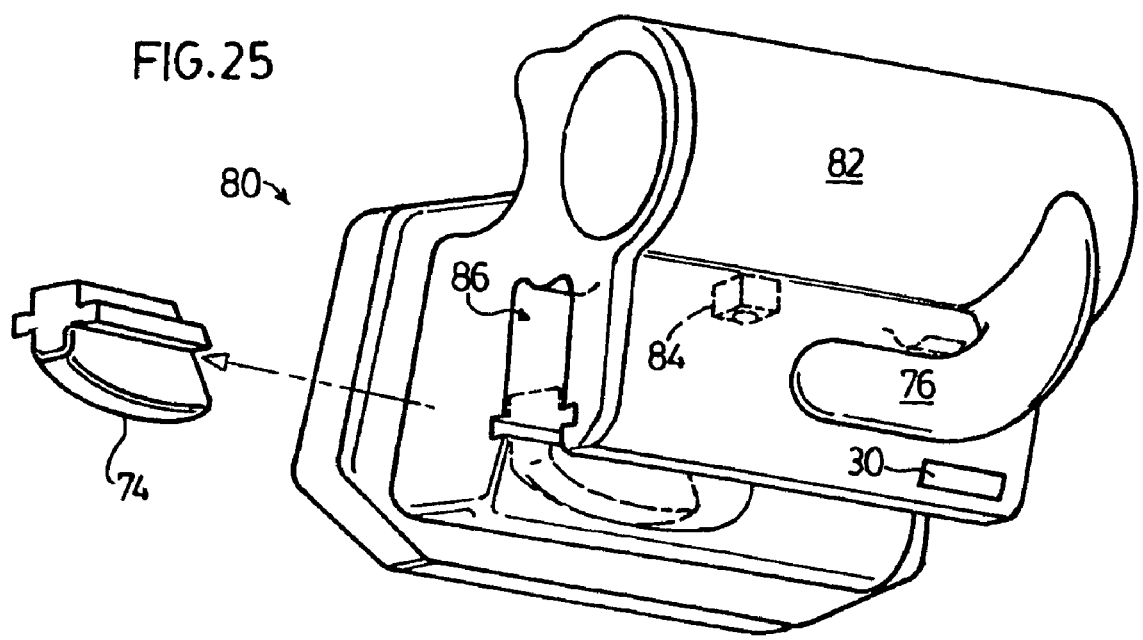
FIG. 25 is a bottom-side perspective view of an upper first molar bracket having a headgear tube, hook and a convertible distal cap.
Figure 26:
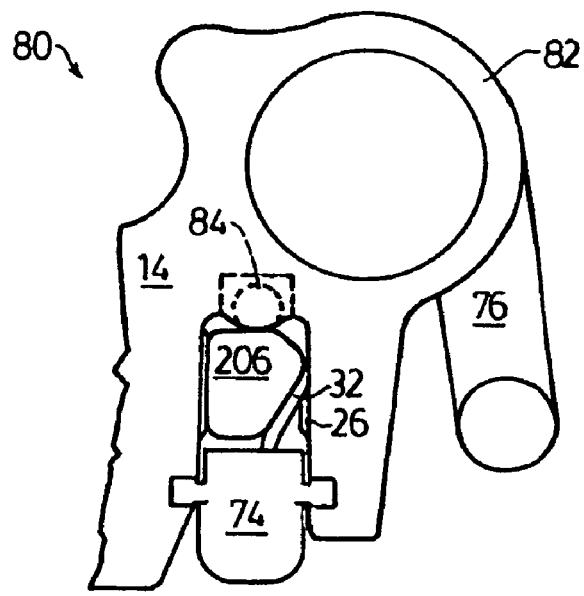
FIG. 26 is a rear-elevational view of the upper first molar bracket of FIG. 25.

FIGS. 25 and 26 show an upper first molar bracket 80 having a buccal headgear tube 82 for receiving an extra-oral device such as headgear, and a convertible buccal tube 72 by virtue of convertible cap 74. Buccal headgear tube 82 is generally round in cross-section and has a diameter opening between 0.045 and 0.051 inches. A roller bearing 84 is seated in slot 86 of bracket 80 to facilitate movement of an archwire within the slot to reduce friction during treatment.

As can be seen, the retention spring functions in conjunction with the walls of the archwire slot to retain an archwire. Where the archwire is large enough, each the spring engages the archwire and provides partial or full seating and accordingly, torque transmission due to being held by an archwire against their rest position bias. The bracket, therefore, either fully seats an archwire in its archwire slot, or more gently moves the tooth appropriately under influence of the spring bias to its correct position.

Figure 27:
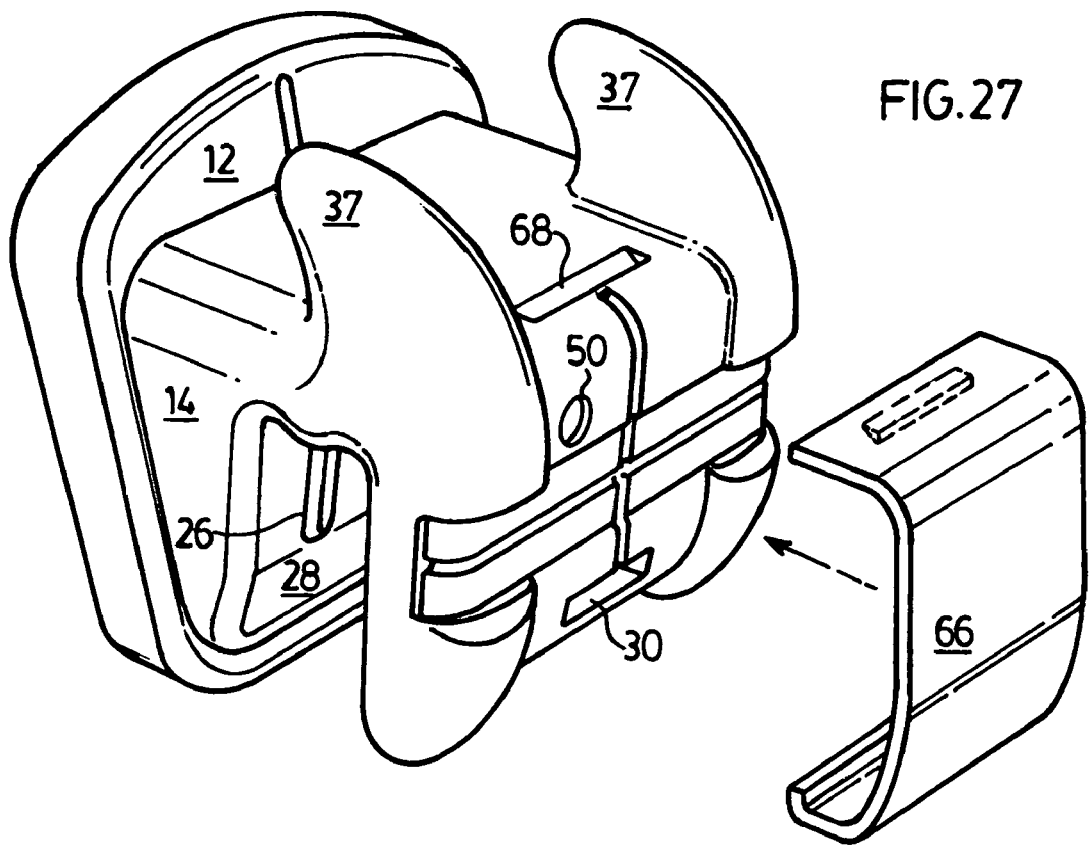
FIG. 27 is a top-side perspective view of a bracket and a bracket cover for attachment thereto.

Referring to FIG. 27, a colored bracket cover 66, molded from a single piece of plastic, metal, rubber, ceramic or combinations thereof may be snapped into a notch 68 in body 14 (bracket 10 shown) or otherwise fitted onto the outside of body 14. Depending on a patient's preference, the colored bracket cover 66 may be tooth-colored for making the bracket less visible, or of another color. As can be seen, bracket cover 66 does not interfere with slot 16 nor interfere with the archwire, and thus does not interfere with the free sliding mechanics in leveling, aligning, or opening and closing of the slot opening 24.

Figure 28:
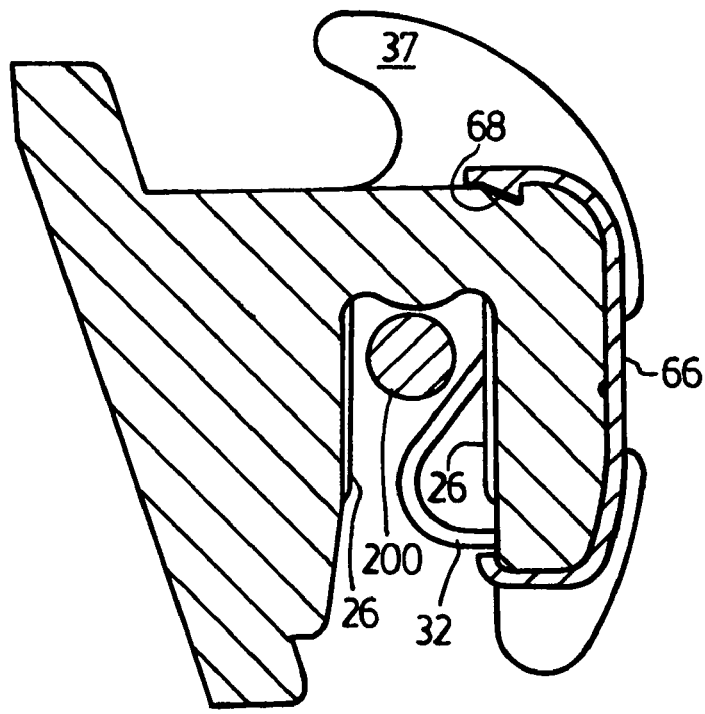
FIG. 28 is a cross-sectional view from the side of a relationship between the bracket cover and the bracket of FIG. 27.
Figure 29A:
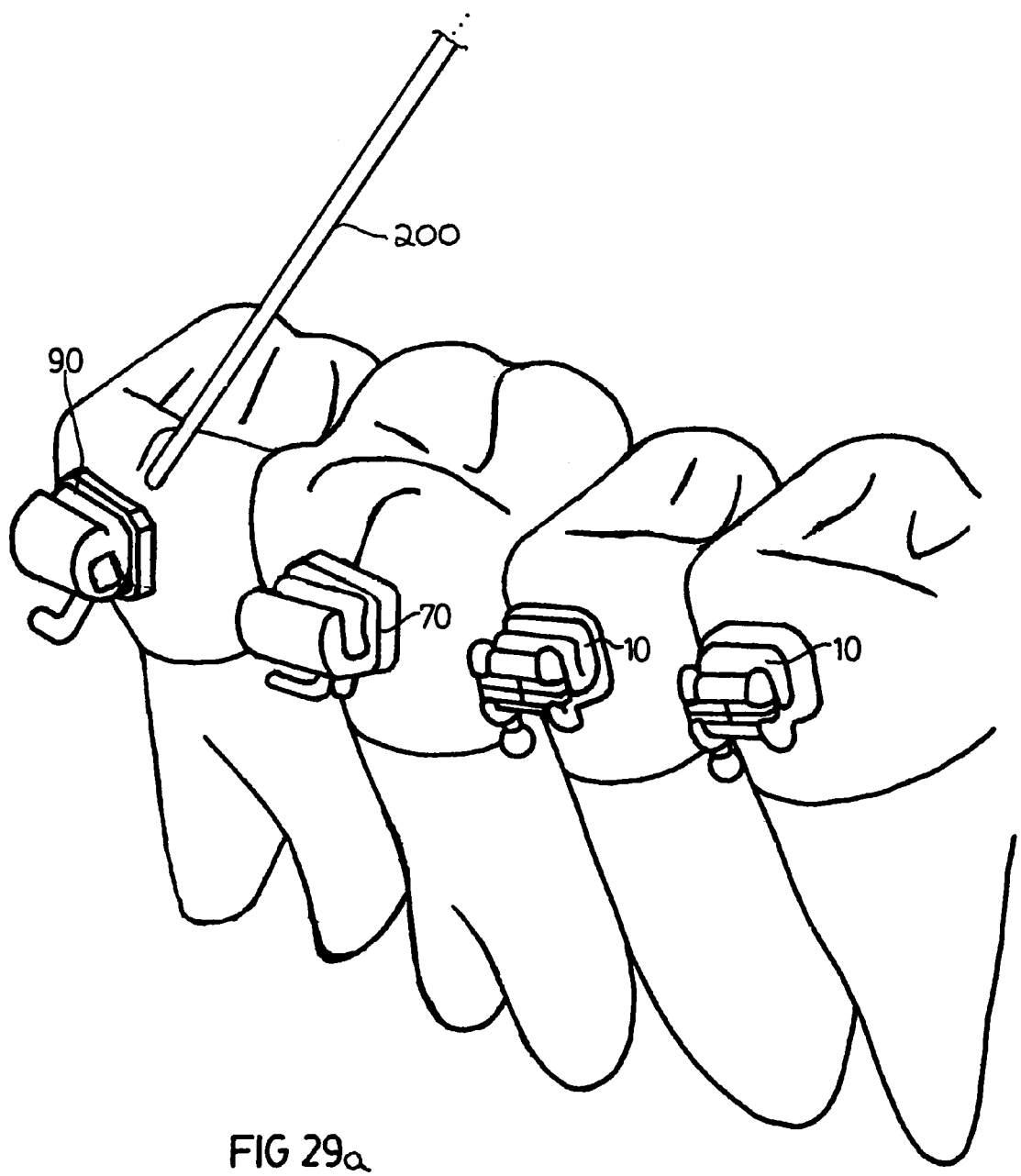
FIGS. 29a–29e are top-side perspective views of a portion of the self-ligating bracket system on a lower arch, each figure showing a successive stage of archwire installation.
Figure 29B:
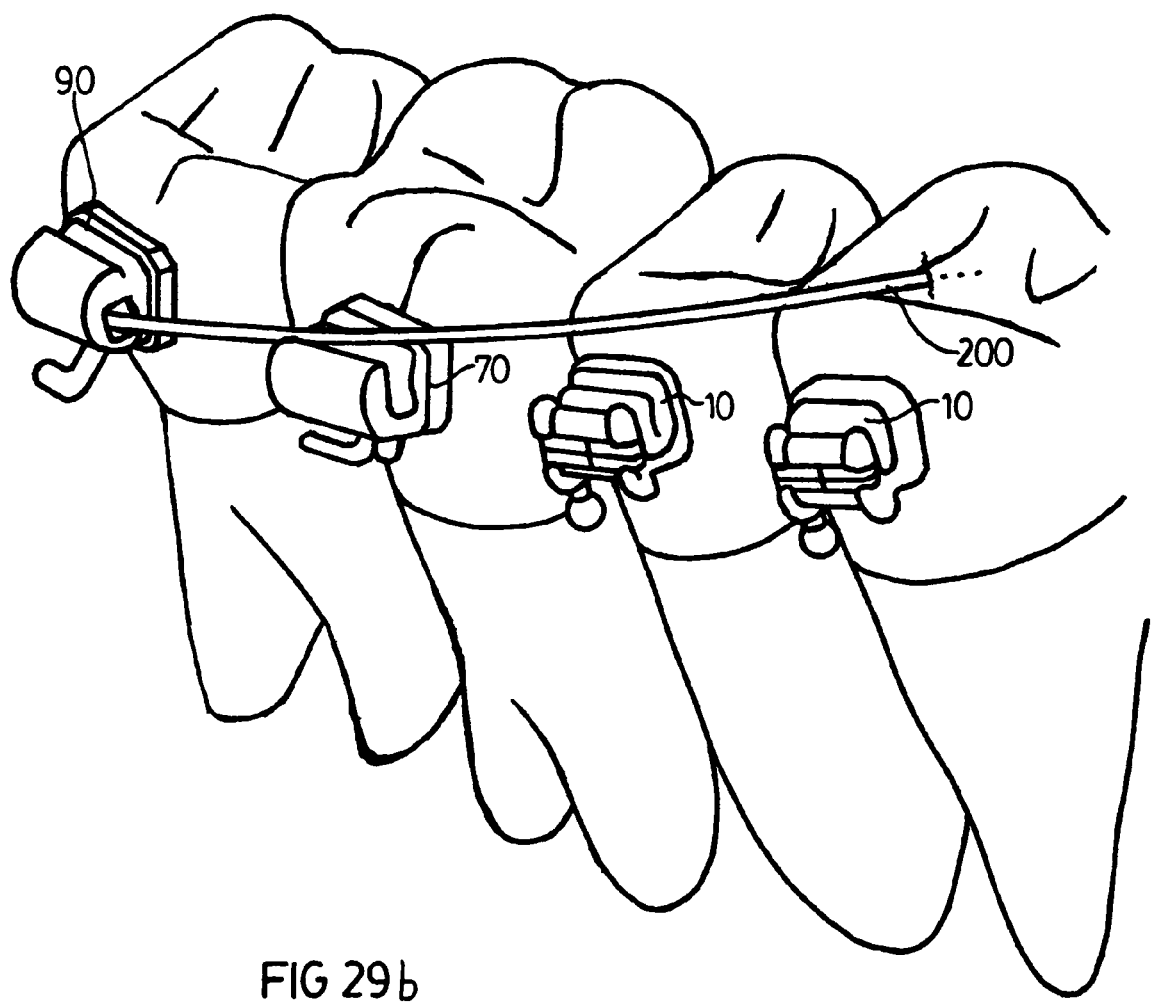
Figure 29:
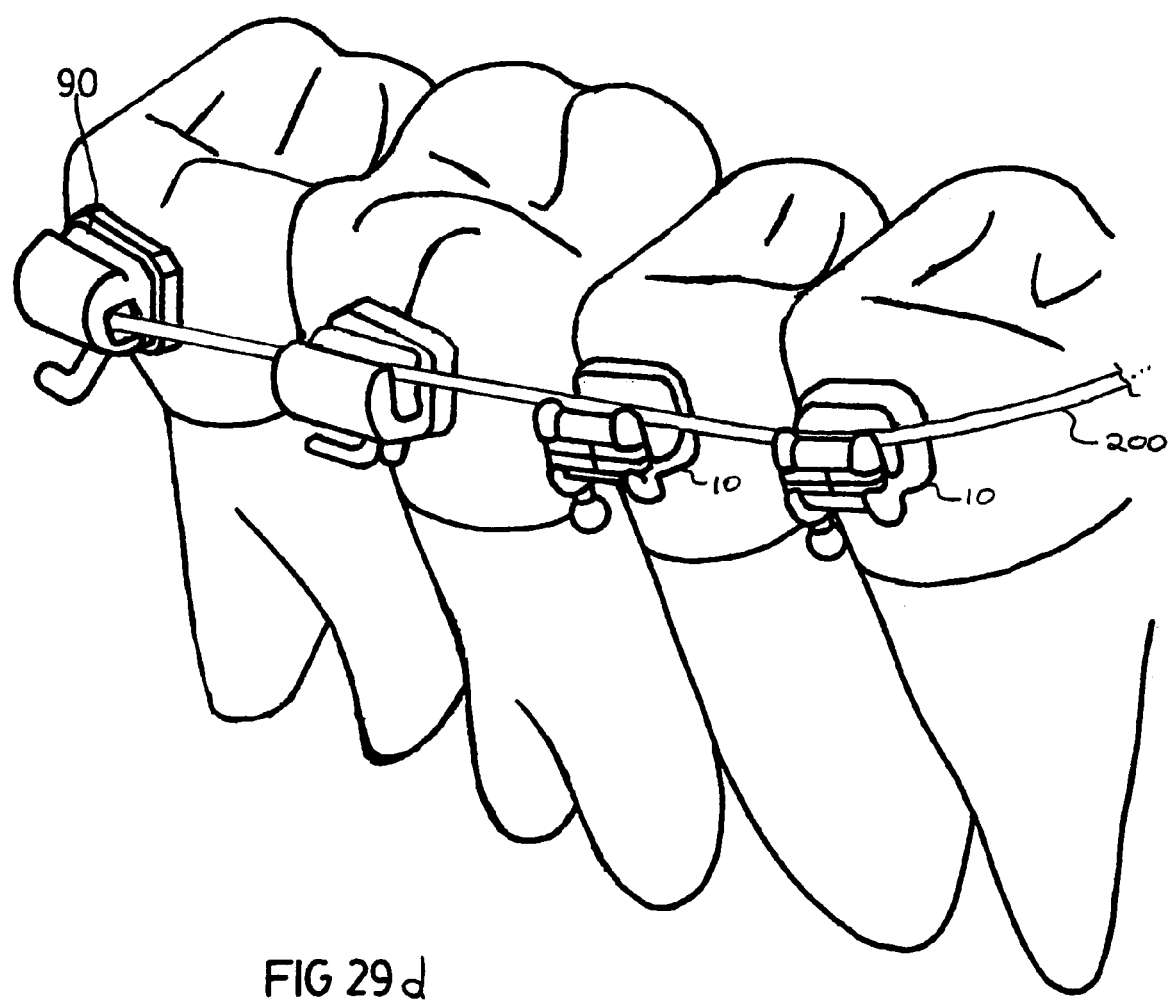
Figure 29:
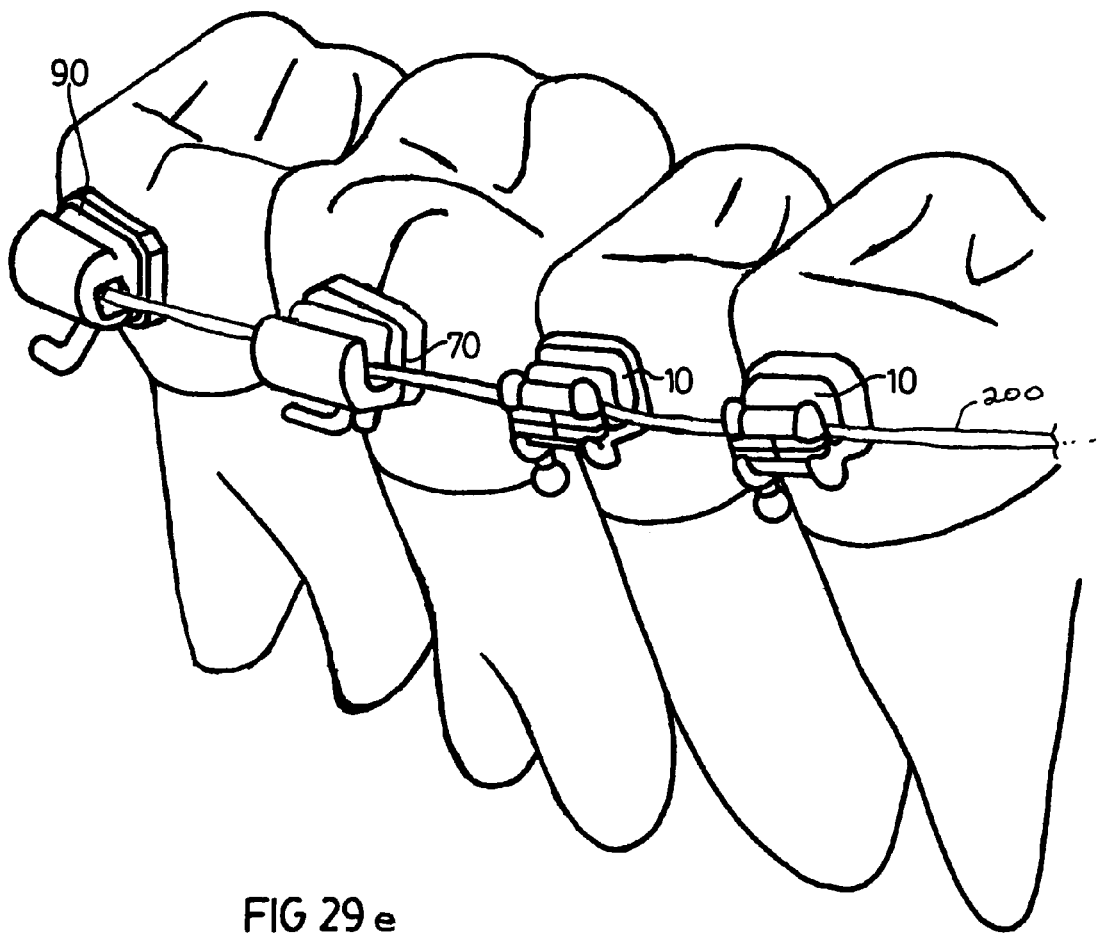

FIG. 28 shows a cutaway side view of the bracket of FIG. 27 and its relationship with the bracket cover 66. It will be understood that other relationships between bracket cover 66 and bracket 10 that enable bracket 10 to be covered in this manner may be conceived.

It will be understood by one of ordinary skill in the art that some patients, particularly children, have not formed $2^{nd}$ molars suitable for appropriate use of a $2^{nd}$ molar bracket. As such, the convertible brackets 70 and 80 bonded to $1^{st}$ molars may be used to "anchor" an archwire. During treatment, the $2^{nd}$ molars may erupt and need to be included in the treatment. In this case, the convertible caps 74 of the convertible brackets 70 and 80 may be removed with a conversion tool to facilitate insertion of an archwire into the $2^{nd}$ molar tubes. Once convertible caps 74 have been removed, the $1^{st}$ molar brackets 70 and 80 operate in a similar manner as brackets 10.

FIGS. 29a–29e show a round archwire 200 being installed into the self-ligating system 5 on a patient's lower arch. The convertible caps 74 are first removed from the two $1^{st}$ molar brackets 70 (only one portion of the arch is shown for ease of understanding), and the two ends of archwire 200 are inserted into respective $2^{nd}$ molar tubes 90. Once its ends are in the $2^{nd}$ molar tubes 90, the arched archwire 200 is pivoted downwards generally about an axis connecting the two $2^{nd}$ molar tubes 90 to progressively enter slots 16 of first the $1^{st}$ molar brackets 70 and then those of successive remaining ones of anterior brackets 10. As the archwire 200 is pivoted to a plane generally parallel with the occlusal plane, it slides into respective bracket slot openings 24 along ramp 28 of lingual wall 20 against the bias of the respective leaf spring 32 (or whichever retention device is being employed). Once the archwire 200 has been pushed sufficiently far into the archwire slots 16, each leaf spring 32 will move back under its bias towards its rest position to retain the archwire 200.

The installation is the same for other types of archwires (such as oval archwire 202, rectangular archwire 204 and 5-sided archwire 206). Depending upon the dimensions of the archwire, leaf spring 32 will either push the archwire against lingual wall 20 and gingival wall 22 in order to seat it within slot 16, or simply move all the way back to its rest position, enclosing but not forcibly seating the archwire within slot 16. Advantageously, there are no individual latches or clips to manipulate, as leaf spring 32 cooperates with archwire slot 16 to retract from slot opening 24 when force in a generally occlusal-gingival direction from an archwire is applied to leaf spring 32.

Figure 30:
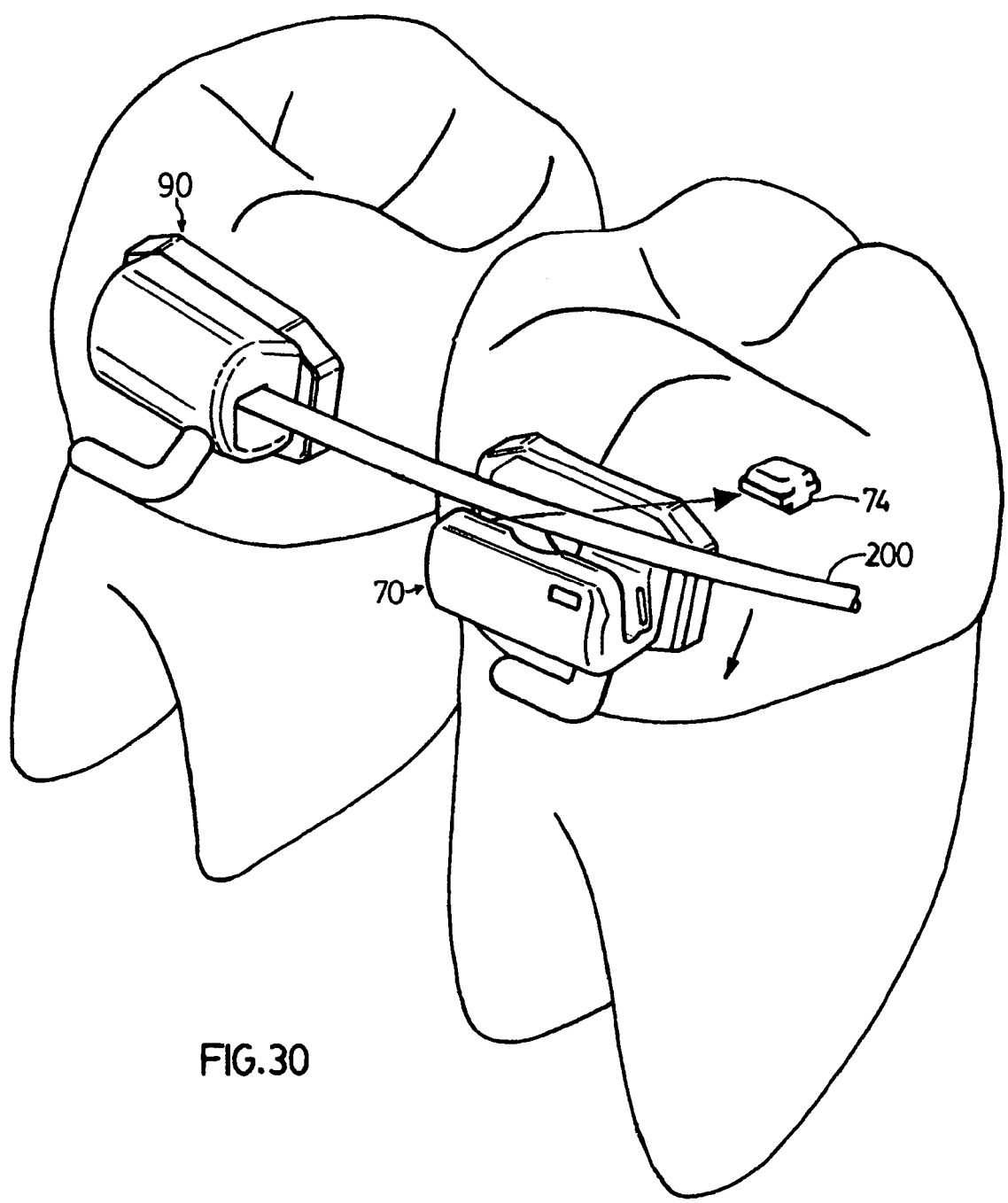
FIG. 30 is a top-side close-up perspective view of a portion of the self-ligating bracket system on a lower arch, showing the archwire inserted into the 2$^{nd}$ molar tube and the 1$^{st}$ molar convertible tube ready to receive the archwire.
Figure 31B:
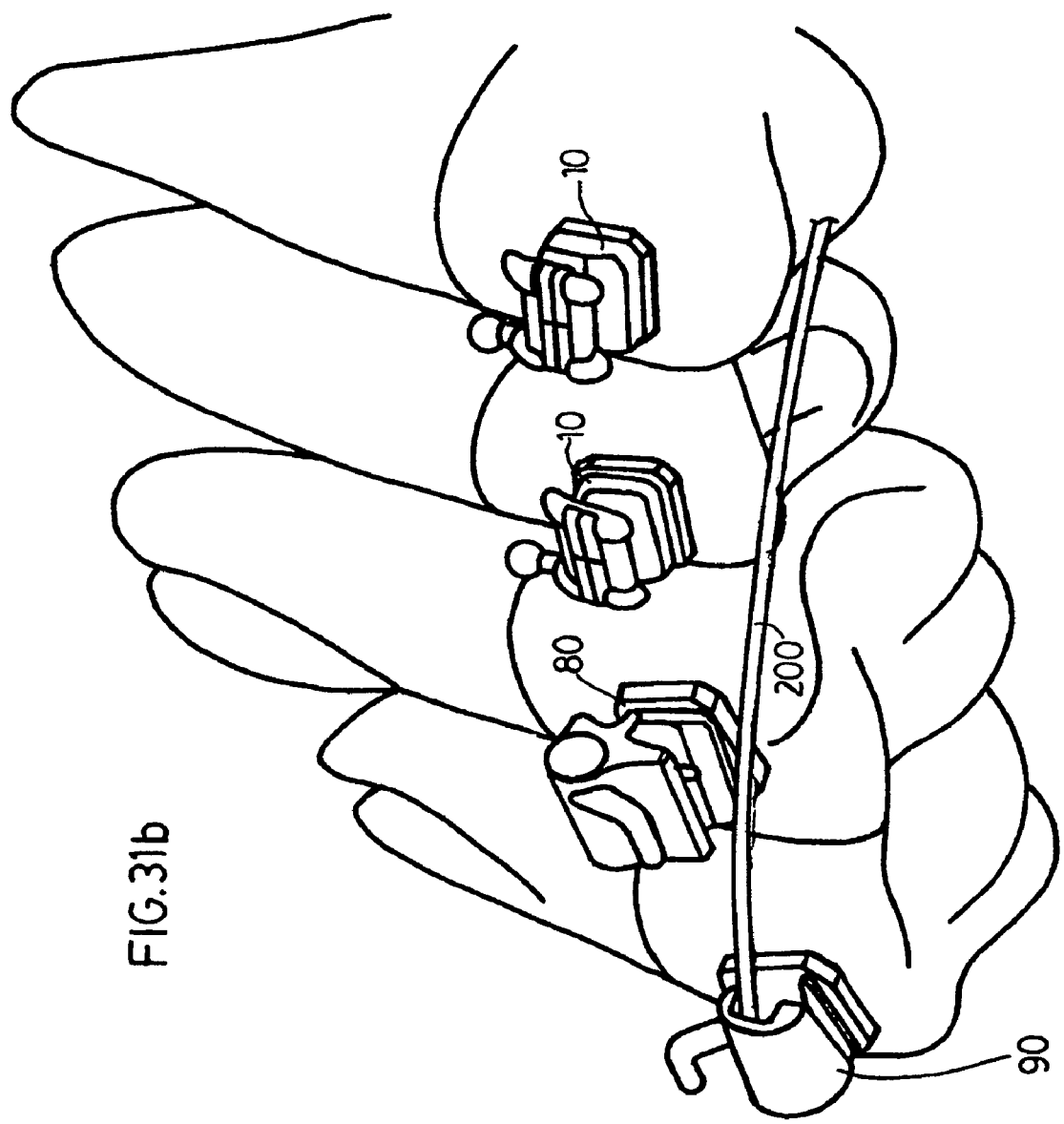
Figure 31C:
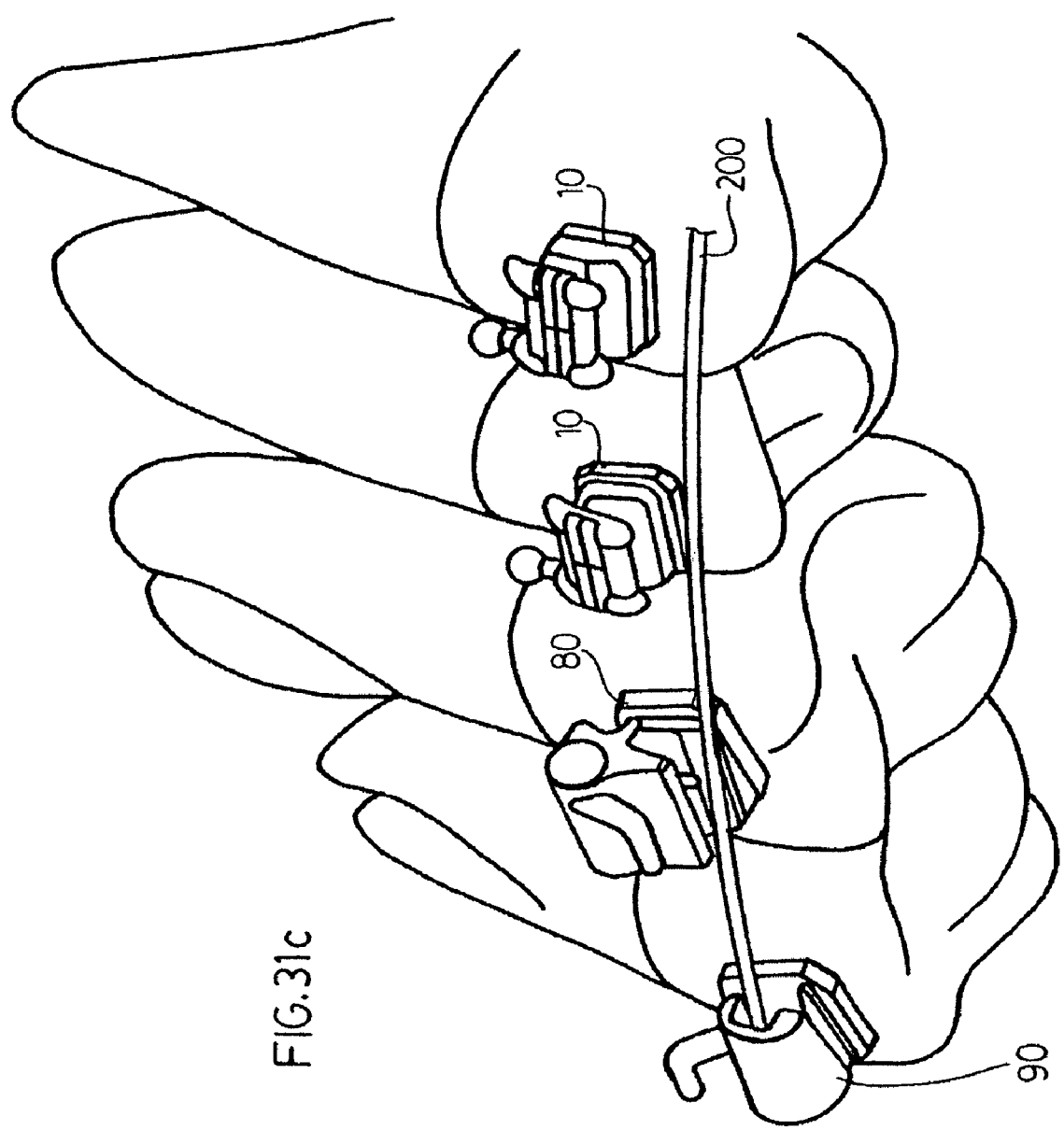
Figure 31D:
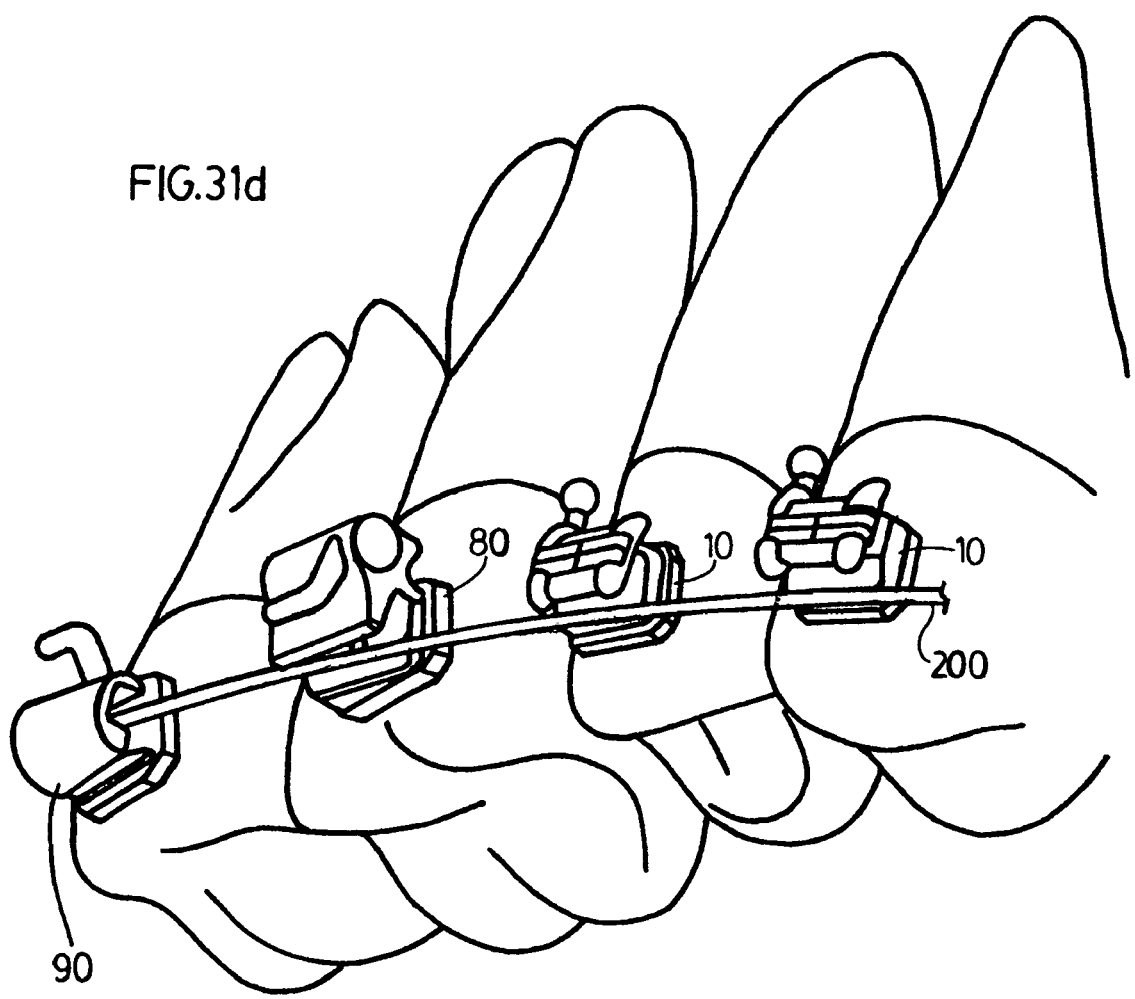
Figure 31E:
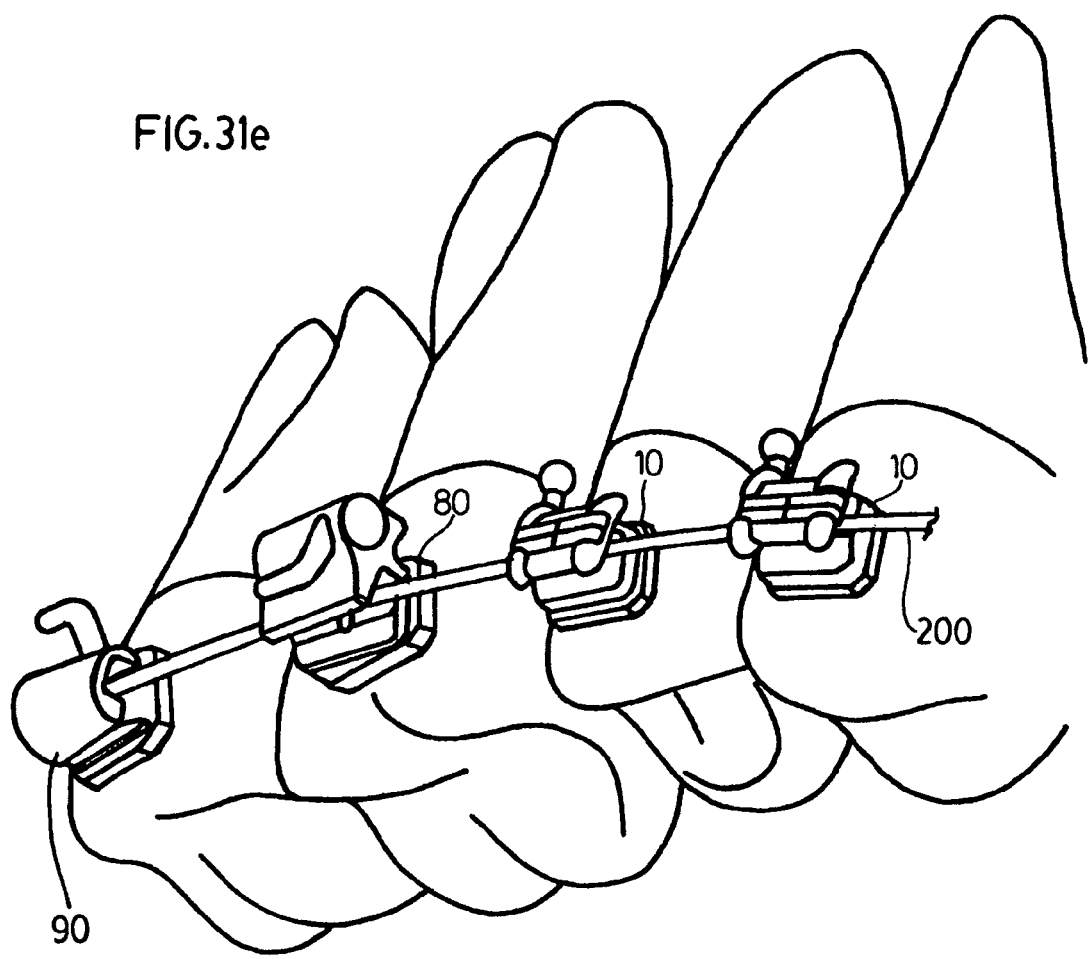

FIG. 30 shows an enlarged perspective top-view of the $2^{nd}$ molar tube 90 and $1^{st}$ molar bracket 70 receiving archwire 200. As can be seen, the convertible cap 74 is removed from $1^{st}$ molar bracket 70 during insertion of archwire 200.

FIGS. 31a–31e show a round archwire 200 being installed into the self-ligating system 5 on a patient's upper arch. The process is the same as insertion of an archwire on a lower arch, as described above. The convertible caps 74 are first removed from the two $1^{st}$ molar brackets 80 (only one is shown for ease of understanding), and the two ends of archwire 200 are inserted into respective $2^{nd}$ molar tubes 90. Once its ends are in the $2^{nd}$ molar tubes 90, the arched archwire 200 is pivoted downwards generally about an axis connecting the two $2^{nd}$ molar tubes 90 to progressively enter slots 16 of first the $1^{st}$ molar brackets 80 and then those of successive remaining ones of anterior brackets 10. As the archwire 200 is pivoted to a plane generally parallel with the occlusal plane, it slides into respective bracket slot openings 24 along ramp 28 of lingual wall 20 against the bias of the leaf spring 32 (or whichever retention device is being employed). Once the archwire 200 has been pushed sufficiently far into the archwire slots 16, each leaf spring 32 will move back under its bias towards its rest position to retain the archwire 200.

A clinician removes an archwire from the upper or lower arch of system 5 by grasping the archwire between the central brackets 10 and pulling down (upper arch) or pulling up (lower arch). As with installation, for removal, individual manipulation of latches or clips is not required, and the entire archwire may be removed in a single movement. In practice, using a Weingart plier, a clinician clutches the archwire in the middle of its arch and pulls it, in a gingival to occlusal direction, out of the slots of the brackets 10 and 80 (70).

Figure 32A:
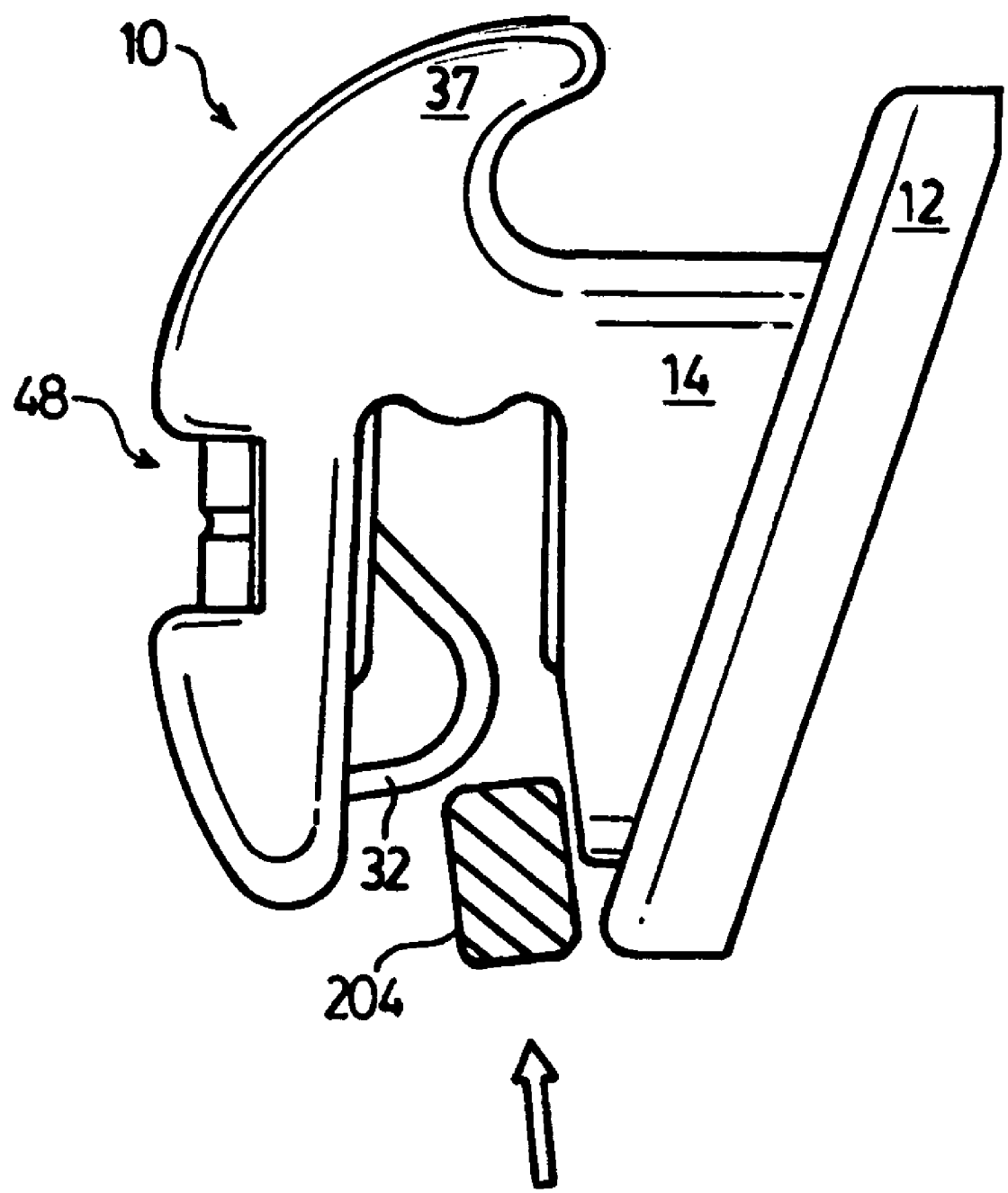
FIGS. 32a–32c are side-elevational views of the bracket of FIG. 2, each figure showing a successive stage of insertion of a rectangular ribbon archwire.
Figure 32B:
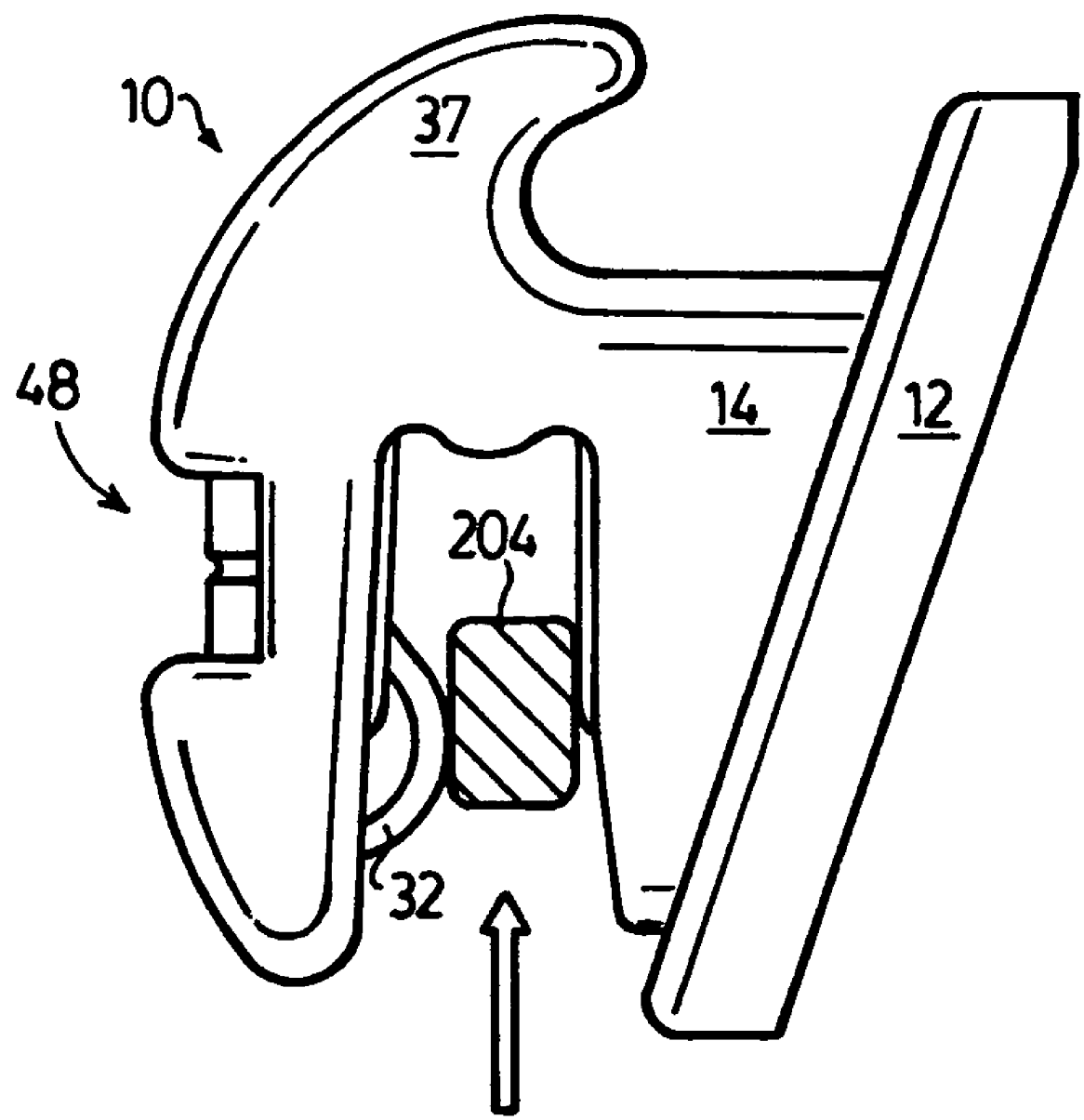
Figure 32C:
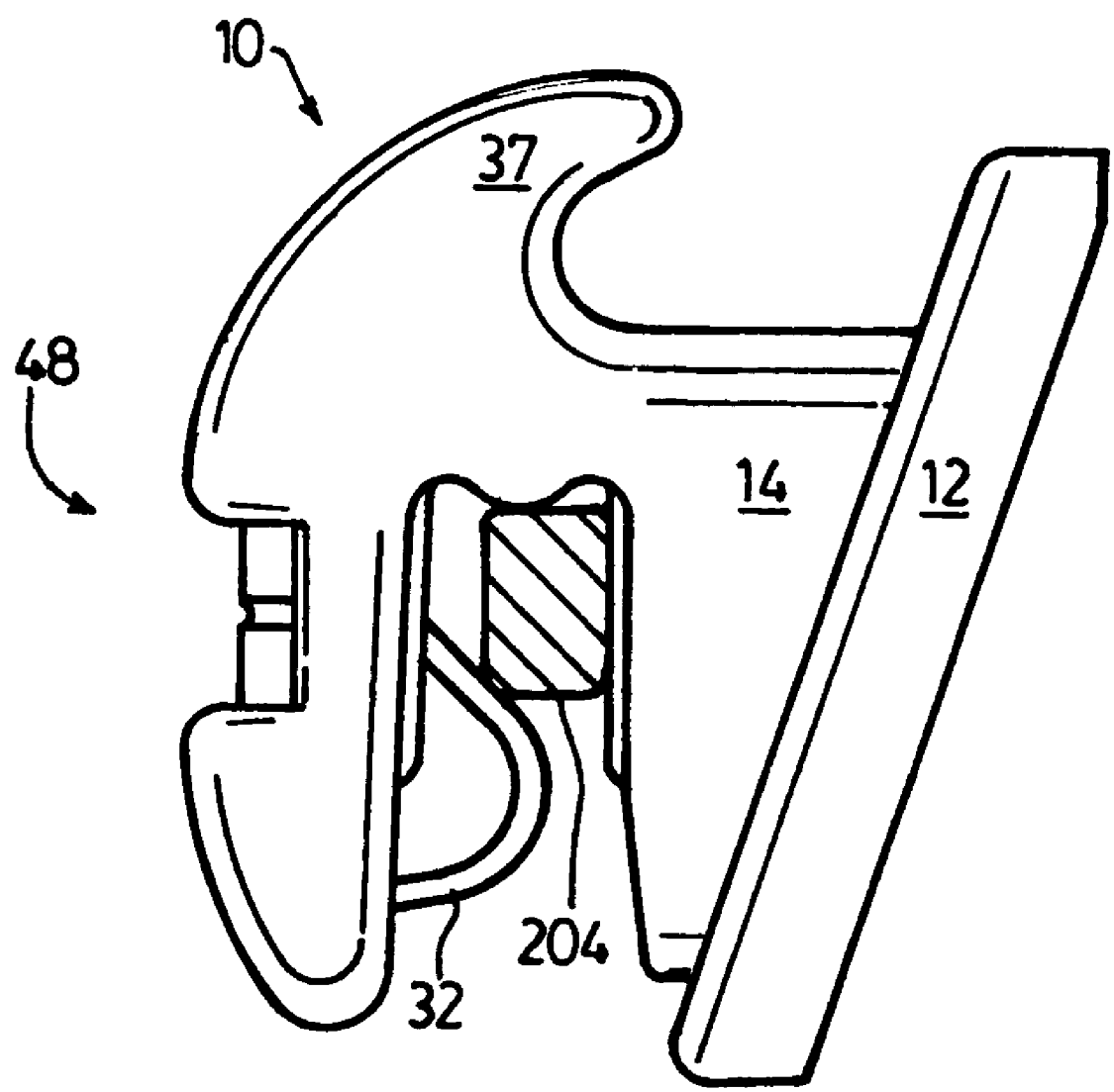

FIGS. 32a–32c are elevational side-views of an embodiment of the bracket 10 showing the successive stages of insertion into bracket 10 of a rectangular ribbon archwire 204 during installation in a self-ligating system 5. As would be clear to one of ordinary skill in the art, removal of archwire 204 is effected in the reverse order as described above.

The shape-memory properties of the Nickel-Titanium (NiTi) leaf spring can be employed to assist with insertion and removal of archwires. Based on the relative amount of nickel to titanium, the NiTi leaf spring will have a transition temperature below which it becomes soft and pliable. As such, a clinician may slightly cool the spring in order to insert an archwire. When the spring becomes warmer that its transition temperature, it assumed its curved shape and can retain an archwire. In a similar manner, removal of the archwire may be facilitated by slightly cooling the spring below its transition temperature in order to make it soft and pliable. Typically, the Ni:Ti ratio will be chosen such that the transition temperature of the NiTi leaf spring is around room temperature.

It will be understood, particularly with reference to the accompanying drawings, that an additional benefit accruing from the embodiments of the present invention described herein is that, because the spring is within the slot and on its inside wall, it is for most practical purposes inaccessible by a patient and also not exposed to patient tissue. This has the advantage of making the system more comfortable than prior art self-ligating designs. While the spring has been shown in the described embodiments on the buccal/labial wall of the slot, it will be understood that the spring may be on, for instance, the lingual wall of the slot.

Although specific embodiments have been described and illustrated, those of skill in the art will appreciate that the variations and modifications may be made without departing from the spirit and scope thereof as defined by the appended claims.

For instance, slotted and wire leaf springs of various configurations have been shown to be particularly elegant and advantageous to the embodiments disclosed herein. However, it will be understood that other spring means such as combinations of coil springs or spring-cushioned ball bearings may function effectively to seat full-sized archwires into the archwire slot, while also being capable of functioning to retain archwires of a range of sizes in the archwire slot. Furthermore, multiple springs of the same or other complementary configurations may be employed in order to achieve the functions described for the archwire retention device. The spring retention device may be received by the bracket in the lingual wall, rather than the buccal/labial wall of the slot.

It will be understood that recess 33 may be formed such that it extends all the way through body 14 from slot 16. This would permit leaf spring 32 to do the same or even extend beyond body 14 to some degree. In the case where leaf spring extends beyond body 14, leaf spring 32 might be annealed and bent back downwards above the point at which it extends beyond body 14, in order to hold it more positively in the bracket 10.

The leaf springs described herein have been formed of a shape memory alloy called nickel-titanium alloy. Such a material is advantageous during manufacture, because when cooled, it is pliable and easy to insert into recess/recesses 33 and niche/niches 30, and also may be cooled in order to facilitate insertion and/or removal of an archwire. When brought back up to body temperature range, the material reverts to its curved shape and assumes its springing properties. However, one of ordinary skill in the art would understand that, for instance, springs of different materials such as steel, chrome-cobalt alloy, titanium-molybdenum alloy, or molded shape-memory plastics would function, and relate to body 14 in much the same manner as described above. Shape-memory plastics, however, are generally required to be warmed above a transition temperature (rather than cooled below a transition temperature as with NiTi) in order to become soft and pliable. As such, a clinician would warm the shape-memory plastic spring or springs in order to facilitate insertion and removal of an archwire.

In the embodiments shown, the spring in its rest position obstructs about 60% of the slot opening. This configuration is advantageous for ease of insertion of an archwire into the slot. During insertion, an archwire can abut the ramp and, because of the combination of partial obstruction and the shape of the spring, push the spring in a buccal/labial direction along the niche. However, within the scope of the invention are embodiments in which the spring could obstruct up to 100% of the opening. It will be understood that configurations of less than 60% obstruction may be used in some embodiments of the invention, providing that the functional aspects of the spring as a retention device are achieved. Of particular note are cases where a shape-memory material is used for the spring, as the shape-memory material may be cooled (or warmed as may be the case if shape-memory plastic) to enable the archwire to enter/exit the slot without requiring the archwire to exert very much force on the spring against its bias during entry/exit.

Furthermore, while the smallest dimension of archwire retained by the retention device in the embodiments disclosed above is 0.014 inches, it will be understood that different situations and applications of the present invention may find need for configurations which permit retaining of smaller archwires. It is also conceivable that, depending on patient requirements or preference of the clinician, the archwire slot of the orthodontic appliance described herein may receive multiple archwires, as would be understood by one of ordinary skill in the art.

What is claimed is:

1. An orthodontic appliance, comprising:
   a base for bonding the appliance to a tooth;
   a body extending from the base;
   an archwire slot extending across the body in a generally mesial-distal direction and opening in a generally occlusal-gingival direction; and
   a resiliently deformable retention device associated with said slot to permit both entry and removal of an archwire from said slot, wherein said retention device comprises a spring for exerting force on a retained archwire having a predetermined minimum dimension, against both a lingual wall and a gingival wall of said archwire slot, wherein said spring is within said archwire slot, wherein a gingival portion of said spring is slidingly received in a recess formed in a buccal/labial wall of said archwire slot.

2. The orthodontic appliance of claim 1, wherein said spring arches from said gingival portion of said spring into an interior of said archwire slot, and then curves away from said slot to terminate at a buccal/labial portion of said spring, said buccal/labial portion of said spring moveable in a generally buccal/labial-lingual direction through a niche formed in said body of said appliance.

3. The orthodontic appliance of claim 2, wherein a lingual wall of said archwire slot is beveled near said archwire slot opening.

4. An orthodontic appliance, comprising:

a base for bonding the appliance to a tooth;

a body extending from the base;

an archwire slot extending across the body in a generally mesial-distal direction and opening in a generally occlusal-gingival direction; and a resiliently deformable retention device associated with said slot to permit both entry and removal of an archwire from said slot;

wherein said retention device comprises a spring for exerting force on a retained archwire having a predetermined minimum dimension, against both a lingual wall and a gingival wall of said archwire slot; wherein said spring is within said archwire slot; and further wherein a gingival portion of said spring is slidingly received in a recess formed in a lingual wall of said archwire slot.

5. An orthodontic appliance, comprising:

a base for bonding the appliance to a tooth;

a body extending from the base;

an archwire slot extending across the body in a generally mesial-distal direction and opening in a generally occlusal-gingival direction; and a resiliently deformable retention device associated with said slot to permit both entry and removal of an archwire from said slot;

wherein said archwire slot has a buccal/labial wall, a gingival wall and a lingual wall; and at least one roller bearing seated in said gingival wall, said roller bearing for providing reduced friction when contacting an archwire.

* * * * *